(12) United States Patent
Peng et al.

(10) Patent No.: US 11,865,149 B2
(45) Date of Patent: Jan. 9, 2024

(54) METHODS AND MATERIALS FOR TREATING CANCER

(71) Applicant: Mayo Foundation for Medical Education and Research, Rochester, MN (US)

(72) Inventors: Kah-Whye Peng, Rochester, MN (US); Stephen James Russell, Rochester, MN (US); Mitesh J. Borad, Tempe, AZ (US); Yumei Zhou, Rochester, MN (US); Amber C. Miller, Eden Prairie, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1130 days.

(21) Appl. No.: 16/310,227

(22) PCT Filed: Jun. 15, 2017

(86) PCT No.: PCT/US2017/037650
§ 371 (c)(1),
(2) Date: Dec. 14, 2018

(87) PCT Pub. No.: WO2017/218757
PCT Pub. Date: Dec. 21, 2017

(65) Prior Publication Data
US 2019/0328805 A1    Oct. 31, 2019

Related U.S. Application Data

(60) Provisional application No. 62/351,768, filed on Jun. 17, 2016.

(51) Int. Cl.
| | | |
|---|---|---|
| *A61K 35/768* | (2015.01) | |
| *G01N 33/574* | (2006.01) | |
| *C12N 7/00* | (2006.01) | |
| *A61K 35/761* | (2015.01) | |
| *A61K 35/763* | (2015.01) | |
| *A61K 35/766* | (2015.01) | |
| *C40B 40/08* | (2006.01) | |

(52) U.S. Cl.
CPC ............ *A61K 35/768* (2013.01); *C12N 7/00* (2013.01); *G01N 33/57438* (2013.01); *A61K 35/761* (2013.01); *A61K 35/763* (2013.01); *A61K 35/766* (2013.01); *C40B 40/08* (2013.01); *G01N 2800/52* (2013.01)

(58) Field of Classification Search
CPC . G01N 2800/52; G01N 33/574–57449; A61K 35/766; A61K 35/76–768
See application file for complete search history.

(56) References Cited

U.S. PATENT DOCUMENTS

2012/0004119 A1    1/2012  Lenburg et al.
2014/0377221 A1   12/2014  Tufaro et al.
2016/0153053 A1    6/2016  Skog et al.

FOREIGN PATENT DOCUMENTS

WO    WO-2009054996 A2 *  4/2009  ........... A61K 35/768

OTHER PUBLICATIONS

NCT01628640 (Version 7, May 19, 2015, 4 pages) (Year: 2015).*
Zoren et al., Clinical Cancer Research, 2003, vol. 9, pp. 4811-4818 (Year: 2003).*
Komatsu et al (Oncogene, 2015, vol. 34, pp. 3985-3993) (Year: 2015).*
cran.r-project.org [online], "Package 'gplots'", Jan. 27, 2019, [retrieved on Jan. 8, 2019], retrieved from:" https://cran.r-project.org/web/packages/gplots/gplots.pdf, 68 pages.
International Search Report & Written Opinion in International Application No. PCT/US2017/037650 dated Nov. 8, 2017, 28 pages.
Jenks et al., "Safety studies on intrahepatic or intratumoral injection of oncolytic vesicular stomatitis virus expressing interferon-β in rodents and nonhuman primates," Human gene therapy, 21(4):451-62, Mar. 2010.
Liu et al., "Clinical trial results with oncolytic virotherapy: a century of promise, a decade of progress, " Nat. Clin. Pract. Oncol., 4(2):101-117, Feb. 2007.
Love et al., "Moderated estimation of fold change and dispersion for RNA-seq data with DESeq2," Genome Biology, 15(12):550, 2014.
Naik and Russell, "Engineering oncolytic viruses to exploit tumor specific defects in innate immune signaling pathways," Expert Opin. Biol. Ther., 9(9):1163-1176, Sep. 2009.
Shen et al., "Immunovirotherapy with vesicular stomatitis virus and PD-L1 blockade enhances therapeutic outcome in murine acute myeloid leukemia," Blood, 127(11):1449-58, Mar. 2016.
Bekisz et al., "Antiproliferative Properties of Type I and Type II Interferon," Pharmaceuticals, Mar. 30, 2010, 3(4):994-1015.
Groettrup et al., "Proteasomes in immune cells: more than peptide producers?," Nat. Rev. Immunology, Dec. 11, 2009, 10(1):73-78.
Oshiumi et al., "DDX60 Is Involved in RIG-I-Dependent and Independent Antiviral Responses, and Its Function Is Attenuated by Virus-Induced EGFR Activation," Cell Reports, May 26, 2015, 11(8):1193-1207.
Xie, "TRAF molecules in cell signaling and in human diseases," J. Mol. Signaling, Jun. 2013, 8:7, 31 pages.
Yang et al., "Toll-like receptors in liver fibrosis: cellular crosstalk and mechanisms," Front. Physiology, May 22, 2012, 3:138.

* cited by examiner

*Primary Examiner* — Karen A. Canella
(74) *Attorney, Agent, or Firm* — Fish & Richardson P.C.

(57) ABSTRACT

This document relates to methods and materials involved in treating cancer. For example, methods and materials for using one or more oncolytic viruses (e.g., one or more replicating oncolytic viruses) to treat cancer in a mammal (e.g., a human) identified as having a cancer likely to respond to oncolytic virotherapy are provided.

20 Claims, 16 Drawing Sheets

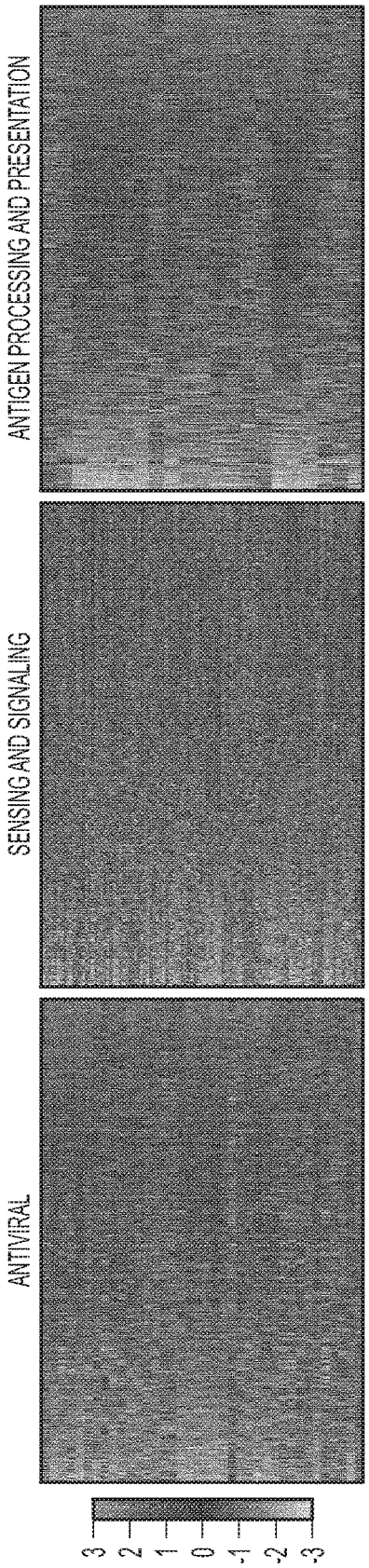
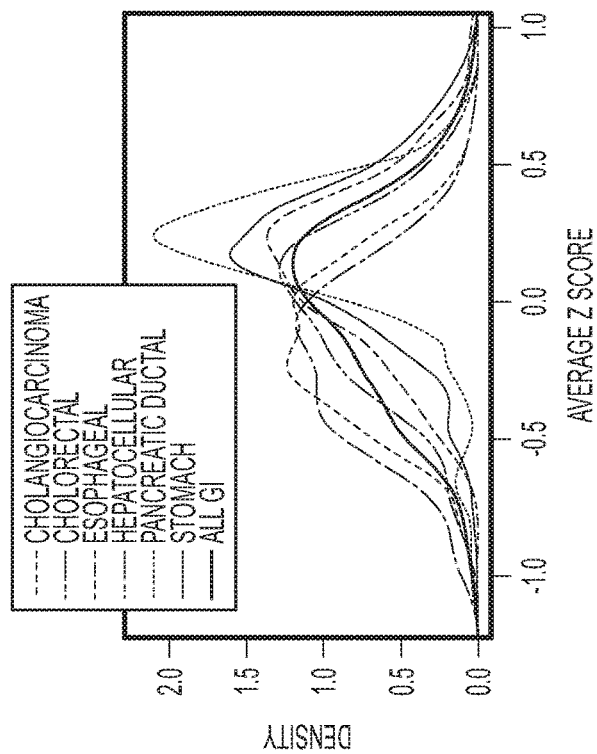
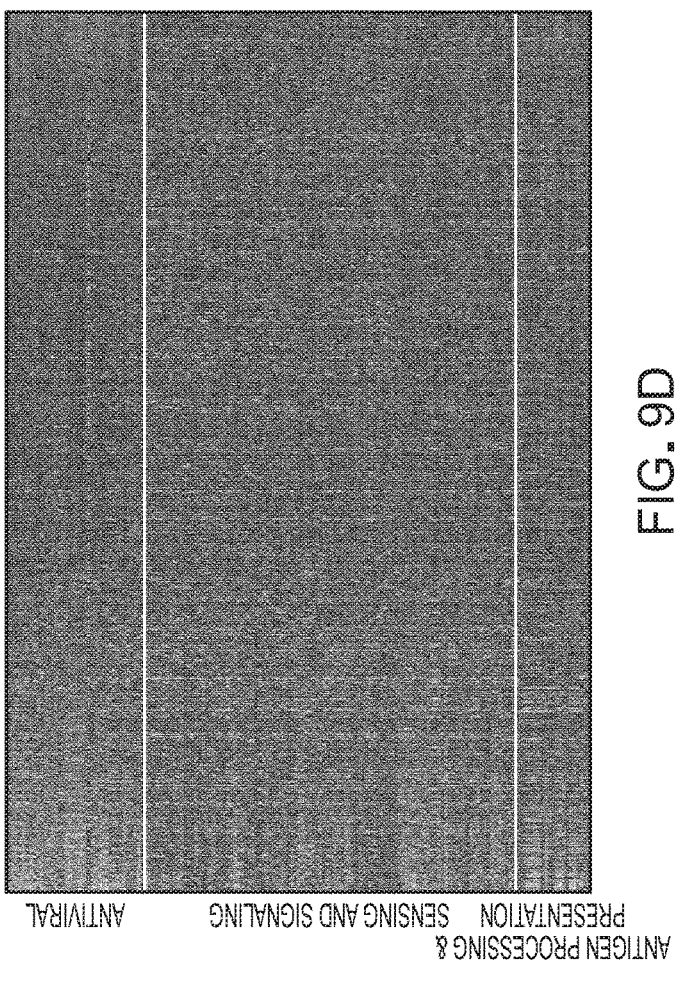
FIG. 9A  FIG. 9B  FIG. 9C  FIG. 9D  FIG. 9E

METHODS AND MATERIALS FOR TREATING CANCER

CROSS-REFERENCE TO RELATED APPLICATIONS

This application is a National Stage application under 35 U.S.C. § 371 of International Application No. PCT/US2017/037650, having an International Filing Date of Jun. 15, 2017, which claims priority to U.S. Application Ser. No. 62/351,768, filed on Jun. 17, 2016. The disclosures of the prior applications are considered part of the disclosure of this application, and are incorporated in their entirety into this application.

BACKGROUND

1. Technical Field

This document relates to methods and materials involved in treating cancer. For example, this document provides methods and materials for using one or more oncolytic viruses (e.g., one or more replicating oncolytic viruses) to treat cancer in a mammal (e.g., a human) identified as having a cancer likely to respond to oncolytic virotherapy.

2. Background Information

Oncolytic viruses are cancer therapies that employ engineered or naturally evolved viruses of cancer tropism to incite tumor cell death in the treated patient. In general, when a replicating oncolytic virus is inoculated into a tumor, infected tumor cells have the potential to produce progeny virus, allowing destructive infection to spread to neighboring tumor cells. The potential for virus replication is determined by the cell's ability to sense and respond to the viral infection, and infection is typically contained such that intratumoral spread and viremic spread to distant sites of tumor growth are both minimal. Occasionally, however, the virus infection spreads rapidly and extensively, both throughout the injected tumor and via the bloodstream to distant tumor deposits. This relatively infrequent outcome of extensive intratumoral viral spread can cause favorable extensive tumor lysis, but also can cause tumor lysis syndrome leading to systemic toxicities that may be fatal if not anticipated.

SUMMARY

This document provides methods and materials for treating cancer. For example, this document provides methods and materials for (a) identifying a mammal as having cancer cells with an anti-viral deficiency based, at least in part, on the presence of a virotherapy permissive gene expression signature and (b) administering one or more oncolytic viruses (e.g., one or more replicating oncolytic viruses) to treat cancer in the mammal (e.g., a human) identified as having an anti-viral deficiency. As described herein, mammals identified as having cancer cells with a virotherapy permissive gene expression signature can be effectively treated with one or more oncolytic viruses effective to kill cancer cells via viral replication. A virotherapy permissive gene expression signature is a gene expression signature that indicates that a cancer cell has significantly low or moderately low expression levels for four gene sets (i.e., Gene Set 1, Gene Set 2, Gene Set 3, Gene Set 4, Gene Set 5, Gene Set 6, and Gene Set 7) as compared to those expression levels observed in control cells (e.g., control cells collected from the mammal's healthy tissue).

This document also provides methods for identifying a mammal as having a cancer that is responsive to treatment with one or more oncolytic viruses. For example, cancer cells obtained from a mammal having cancer can be assessed to determine if they have an anti-viral deficiency based, at least in part, on the presence of a virotherapy permissive gene expression signature. If the cancer cells have an anti-viral deficiency based, at least in part, on the presence of a virotherapy permissive gene expression signature, then the mammal can be classified as having a cancer responsive to treatment with one or more oncolytic viruses effective to kill cancer cells via viral replication. If the cancer cells do not have a virotherapy permissive gene expression signature, then the mammal can be classified as having a cancer that is not responsive to treatment with an oncolytic virus as the sole anti-cancer treatment agent via viral replication. Such a mammal can be treated with, for example, repeated high dose administrations (e.g., intratumoral injections) of oncolytic viruses as immunotherapy agents.

As described herein, there is a need in the field of oncolytic virotherapy for a test that can determine whether or not an administered oncolytic virus will spread rapidly and extensively in the tumor tissue of a given patient prior to treatment in order to identify the likelihood of viral replication and to anticipate tumor lysis syndrome. The methods and materials described herein provide such a test.

In general, one aspect of this document features a method for treating cancer in a mammal. The method comprises, or consists essentially of, (a) identifying the mammal as having cancer cells that have a virotherapy permissive gene expression signature, and (b) administering an oncolytic virus to the mammal under conditions wherein the number of cancer cells within the mammal is reduced. The mammal can be a human. The cancer can be liver cancer. The cancer cells can express a low level of a majority of the genes of Gene Set 1, Gene Set 2, Gene Set 3, and Gene Set 4 of Table 1 as compared to control cells and/or a low level of a majority of the genes of Gene Set 5, Gene Set 6, and Gene Set 7 of Table 2 as compared to control cells. The control cells can be normal, healthy cells. The oncolytic virus can be VSV-IFNβ. The method can comprise administering the oncolytic virus to the mammal no more than one time.

In another aspect, this document features a method for identifying a mammal as having cancer susceptible to treatment with an oncolytic virus. The method comprises, or consists essentially of, (a) determining that cancer cells of the cancer have a virotherapy permissive gene expression signature, and (b) classifying the mammal as having cancer susceptible to treatment with the oncolytic virus. The mammal can be a human. The cancer can be liver cancer. The cancer cells can express a low level of a majority of the genes of Gene Set 1, Gene Set 2, Gene Set 3, and Gene Set 4 of Table 1 as compared to control cells and/or a low level of a majority of the genes of Gene Set 5, Gene Set 6, and Gene Set 7 of Table 2 as compared to control cells. The control cells can be normal, healthy cells. The oncolytic virus can be VSV-IFNβ.

In another aspect, this document features a method for treating cancer in a mammal, wherein the method comprises, or consists essentially of, (a) identifying the mammal as having cancer cells that lack low expression of at least 50 percent of the genes for each of Gene Sets 1-4 of Table 1 and/or at least 50 percent of the genes for each of Gene Sets 5-7 of Table 2, and (b) administering an oncolytic virus, to the mammal, at a dose of $1\times10^9$ TCID$_{50}$ or greater and at least once every two to four weeks for a total of at least two administrations to induce an immune response against the cancer, wherein the number of cancer cells within the mammal is reduced. The mammal can be a human. The cancer can be liver cancer. The cancer cells can be cells that do not express a low level of a majority of the genes of Gene Set 1, Gene Set 2, Gene Set 3, and Gene Set 4 of Table 1 as compared to control cells and/or a low level of a majority of the genes of Gene Set 5, Gene Set 6, and Gene Set 7 of Table 2 as compared to control cells. The control cells can be normal, healthy cells. The oncolytic virus can be VSV-IFNβ. The method can comprise administering the oncolytic virus to the mammal at least three times.

In another aspect, this document features a method for identifying a mammal as having cancer susceptible to treatment with an oncolytic virus as an immunotherapy, wherein the method comprises, or consists essentially of, (a) determining that cancer cells of the cancer lack low expression of at least 50 percent of the genes for each of Gene Sets 1-4 of Table 1 and/or at least 50 percent of the genes for each of Gene Sets 5-7 of Table 2, and (b) classifying the mammal as having cancer susceptible to treatment with the oncolytic virus as an immunotherapy. The mammal can be a human. The cancer can be liver cancer. The cancer cells can be cells that do not express a low level of a majority of the genes of Gene Set 1, Gene Set 2, Gene Set 3, and Gene Set 4 of Table 1 as compared to control cells and/or a low level of a majority of the genes of Gene Set 5, Gene Set 6, and Gene Set 7 of Table 2 as compared to control cells. The control cells can be normal, healthy cells. The oncolytic virus can be VSV-IFNβ.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 9A-E show the distribution of gene expression within a large population of gastrointestinal (GI) cancers from publicly available RNAseq using gene set pathways for antiviral pathways, filtered for functionality and variability. (A) Standardized expression (relative to mean expression of the same gene in the whole population) of antiviral genes in 1507 GI tumors. Columns were ordered by cumulative sum of standardized expression. (B) Standardized expression (relative to mean expression of the same gene in the whole population) of sensing and signaling genes in 1507 GI tumors (includes RIG-I, TLR, STING, and JAK/STAT). Columns were ordered by cumulative sum of standardized expression. (C) Standardized expression (relative to mean expression of the same gene in the whole population) of antigen processing and presentation genes in 1507 GI tumors. Columns were ordered by cumulative sum of standardized expression. (D) To investigate how these patterns of expression in these three functional classes compare within patients, standardized expression of all genes were shown with columns ordered by cumulative sum of antiviral gene expression. There was a general pattern that patients with low expression of antiviral genes also tended to have low expression of sensing and signaling and antigen processing and presentation genes. (E) There are some differences in the distribution of expression dependent on cancer lineage that may suggest some cancers may be more susceptible to OV than others.

DETAILED DESCRIPTION

Figure 1:
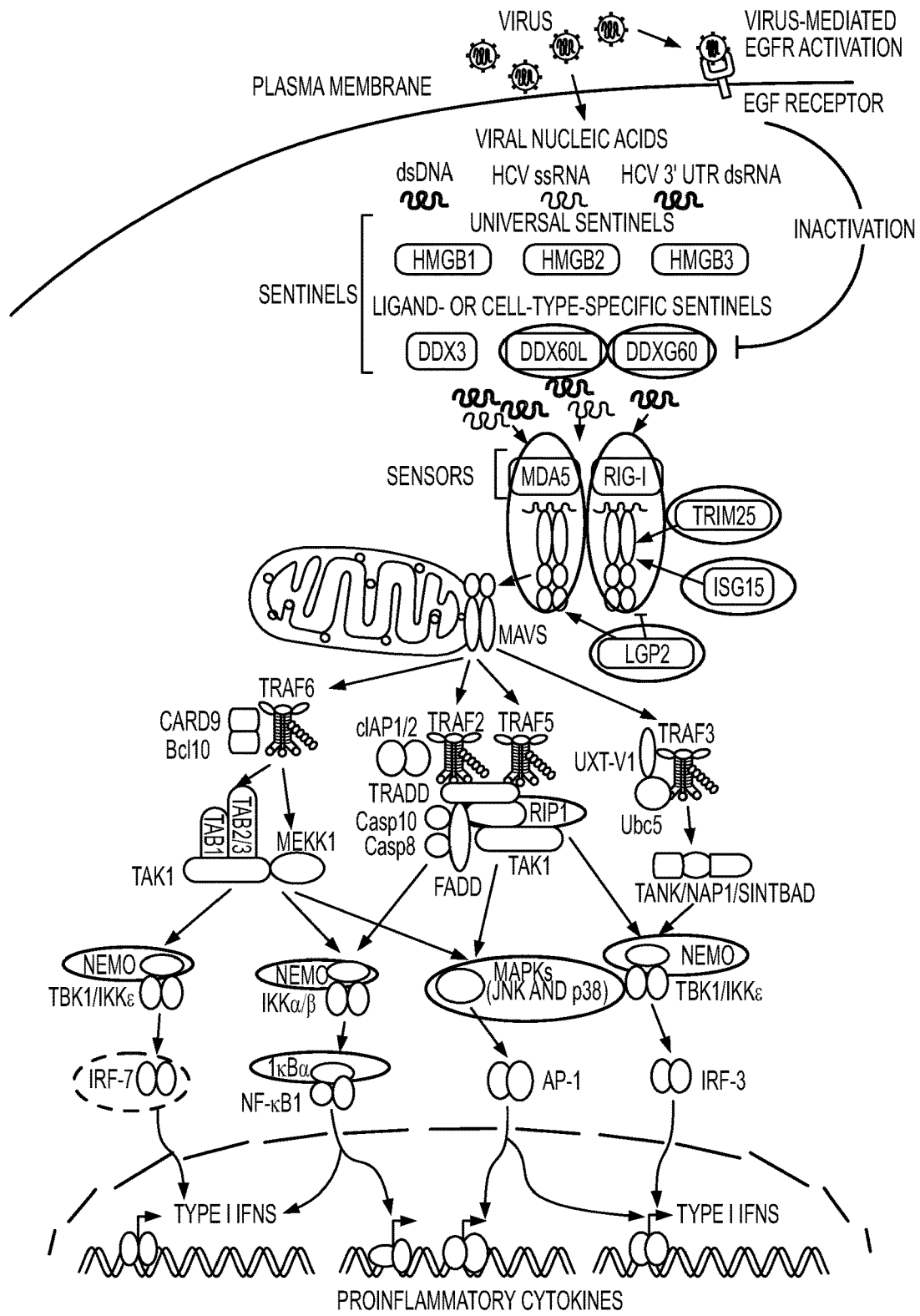
FIG. 1 is a diagram of a molecular RIG-I like receptor (RLR) signaling pathway involved in antiviral responses. Virus entry is detected by protein sentinels that respond to cytoplasmic viral genomes. Sentinels stimulate the sensor proteins that initiate a signaling cascade involving MAPK and/or IKK signaling pathways to stimulate the production of anti-viral genes including IFN and inflammatory cytokines. Solid black ovals indicate proteins identified to have significantly decreased expression in patient 12, relative to the other 11 patients of the cohort. Dashed black ovals indicate proteins essential to the pathway with decreased expression relative to the cohort.

This document provides methods and materials for treating cancer. For example, this document provides methods and materials for (a) identifying a mammal as having cancer cells with an anti-viral deficiency based, at least in part, on the presence of a virotherapy permissive gene expression signature and (b) administering one or more oncolytic viruses (e.g., one or more replicating oncolytic viruses) to treat the mammal identified as having cancer cells with an anti-viral deficiency. Any appropriate mammal having cancer can be treated as described herein. For example, humans and other primates such as monkeys having cancer can be identified as having cancer cells with an anti-viral deficiency and treated with one or more oncolytic viruses to reduce the number of cancer cells present within the human or other primate. In some cases, dogs, cats, horses, cows, pigs, sheep, mice, and rats can be identified and treated with one or more oncolytic viruses as described herein.

Any appropriate cancer can be assessed for an anti-viral deficiency and, if present, treated as described herein. For example, breast cancer, ovarian cancer, osteosarcoma, lung cancer, prostate cancer, liver cancer, pancreatic cancer, brain/CNS tumors, colon cancer, rectal cancer, colorectal cancer, cervical cancer, melanoma, or hematologic malignancies such as multiple myeloma can be assessed for reduced anti-viral activities and treated with one or more oncolytic viruses as described herein.

Any appropriate method can be used to identify a mammal having cancer. For example, imaging techniques and biopsy techniques can be used to identify mammals (e.g., humans) having cancer.

Once identified as having cancer, the cancer can be assessed to determine if the cancer cells have an anti-viral deficiency or a reduced anti-viral activity. Any appropriate method can be used to identify cancer cells as having an anti-viral deficiency or a reduced anti-viral activity. For example, mRNA-based assays such as RT-PCR, RNA capture array, and RNA sequencing (RNAseq) techniques can be used to determine if cancer cells have significantly low or moderately low expression level scores for four gene sets (i.e., Gene Set 1, Gene Set 2, Gene Set 3, Gene Set 4, Gene Set 5, Gene Set 6, and Gene Set 7) as compared to those expression level scores observed in control cells. Examples of control cells include normal, healthy cells comparable to the cancer cell being assessed. For example, if assessing liver cancer cells, then normal, healthy liver cells can be used as control cells. In some cases, peripheral blood mononuclear cells can be used a control cells. In some cases, polypeptide-based assays such as antibody staining techniques or ELISAs can be performed to determine if cancer cells have significantly low or moderately low expression level scores for four gene sets (i.e., Gene Set 1, Gene Set 2, Gene Set 3, Gene Set 4, Gene Set 5, Gene Set 6, and Gene Set 7) as compared to those expression level scores observed in control cells.

Once identified as having cancer cells with an anti-viral deficiency or a reduced anti-viral activity, the mammal can be administered or instructed to self-administer one or more oncolytic viruses to reduce the number of cancer cells present within the mammal. Examples of oncolytic viruses include, without limitation, VSV-IFNβ (Naik and Russell, *Expert Opin. Biol. Ther.,* 9:1163-1176 (2009)) and other forms of engineered or naturally-evolved VSV, adenoviruses, herpes simplex viruses, parvoviruses, vaccinia viruses, Newcastle disease viruses, measles viruses, reoviruses, coxsackie viruses, Seneca valley viruses, and polioviruses (see, e.g., Liu et al., *Nat. Clin. Pract. Oncol.,* 4(2):101-117 (2007)). In some cases, two or more oncolytic viruses (e.g., two, three, four, five, or more oncolytic viruses) can be administered to a mammal to reduce the number of cancer cells present within the mammal.

In some cases, one or more oncolytic viruses can be administered to a mammal once or multiple times over a period of time ranging from days to weeks. In some cases, one or more oncolytic viruses can be formulated into a pharmaceutically acceptable composition for administration to a mammal having cancer. For example, a therapeutically effective amount of an oncolytic virus (e.g., VSV-IFNβ) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more oncolytic viruses can be designed for oral, parenteral (including subcutaneous, intramuscular, intravenous, and intradermal), or intratumoral administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more oncolytic viruses can be administered locally (e.g., intratumorally) or systemically. For example, a composition provided herein can be administered locally by injection into tumors. In some cases, a composition provided herein can be administered systemically, orally, or by injection to a mammal (e.g., a human).

Effective doses can vary depending on the severity of the cancer, the route of administration, the age and general health condition of the subject, excipient usage, the possibility of co-usage with other therapeutic treatments such as use of other agents, and the judgment of the treating physician.

An effective amount of a composition containing one or more oncolytic viruses can be any amount that reduces the number of cancer cells present within the mammal without producing significant toxicity to the mammal. For example, an effective amount of an oncolytic virus such as VSV-IFNβ can be from about $1\times10^5$ TCID$_{50}$ (tissue culture infective dose) per dose to about $1\times10^9$ TCID$_{50}$ per dose (e.g., from about $1\times10^6$ TCID$_{50}$ per dose to about $1\times10^9$ TCID$_{50}$ per dose, from about $1\times10^7$ TCID$_{50}$ per dose to about $1\times10^9$ TCID$_{50}$ per dose, from about $1\times10^8$ TCID$_{50}$ per dose to about $1\times10^9$ TCID$_{50}$ per dose, or from about $1\times10^7$ TCID$_{50}$ per dose to about $1\times10^8$ TCID$_{50}$ per dose). In some cases, from about $1\times10^5$ TCID$_{50}$ to about $1\times10^9$ TCID$_{50}$ (e.g., from about $1\times10^6$ TCID$_{50}$ to about $1\times10^9$ TCID$_{50}$, from about $1\times10^7$ TCID$_{50}$ to about $1\times10^9$ TCID$_{50}$, from about $1\times10^8$ TCID$_{50}$ to about $1\times10^9$ TCID$_{50}$, or from about $1\times10^7$ TCID$_{50}$ to about $1\times10^8$ TCID$_{50}$) of an oncolytic virus such as VSV-IFNβ can be administered directly into a tumor of a human.

If a particular mammal fails to respond to a particular amount, then the amount of an oncolytic virus can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of an oncolytic virus can be any amount that reduces the number of cancer cells present within the mammal without producing significant toxicity to the mammal. For example, the frequency of administration of an oncolytic virus can be from about two to about three times a week to about two to about three times a month. In some cases, a mammal having cancer identified as having an anti-viral deficiency or a reduced anti-viral activity can receive a single administration of an oncolytic virus. The frequency of administration of an oncolytic virus can remain constant or can be variable during the duration of treatment. A course of treatment with a composition containing an oncolytic virus can include rest periods. For example, a composition containing one or more oncolytic viruses can be administered every other month over a two year period followed by a six month rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more oncolytic viruses can be any duration that reduces the number of cancer cells present within the mammal without producing significant toxicity to the mammal. In some cases, the effective duration can vary from several months to several years. In general, the effective duration for reducing the number of cancer cells present within the mammal can range in duration from about one or two months to five or more years. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment, the number of cancer cells present within a mammal, and/or the severity of one or more symptoms related to the condition being treated (e.g., cancer) can be monitored. Any appropriate method can be used to determine whether or not the number of cancer cells present within a mammal is reduced. For example, imaging techniques can be used to assess the number of cancer cells present within a mammal.

As described herein, a comprehensive tumor and normal tissue RNAseq data set available from a cohort of VSV-IFNβ treated patients was used to determine a gene expression profile or gene signature (e.g., a virotherapy permissive gene expression signature) that can predict the possibility of extensive intratumoral virus spread before administering the oncolytic viruses. In some cases, cancer cells can have a virotherapy permissive gene expression signature when those cancer cells exhibit low expression level scores for four gene sets (i.e., Gene Set 1, Gene Set 2, Gene Set 3, and Gene Set 4) as compared to the scores observed for comparable control cells. The genes for each of the four gene sets (Gene Sets 1-4) are set forth in Table 1. In some cases, cancer cells can have a virotherapy permissive gene expression signature when those cancer cells exhibit low expression level scores for three gene sets (i.e., Gene Set 5, Gene Set 6, and Gene Set 7) as compared to the scores observed for comparable control cells. The genes for each of the three gene sets (Gene Sets 5-7) are set forth in Table 2.

TABLE 1

| Gene Set | Signature Group | Gene Name | Alias | FIG. | Example z score |
|---|---|---|---|---|---|
| 1 | Antiviral state | IFI27 | | | -2.79188 |
| | | IFI27L1 | | | -3.02094 |
| | | IFI30 | | | -3.0013 |
| | | IFI6 | | | -3.74032 |
| | | IFI35 | | | -5.31129 |
| | | IFI16 | | | -2.21378 |
| | | IFI44 | | | -3.314 |
| | | IFIT3 | | | -5.17781 |
| | | IFIT2 | | | -3.29947 |
| | | IFIT1 | | | -4.07876 |
| | | IFIT1B | | | -2.81238 |
| | | IFIT5 | | | -7.6971 |
| | | IFITM3 | | | -3.45001 |
| | | TRIM14 | | | -2.16373 |

TABLE 1-continued

| Gene Set | Signature Group | Gene Name | Alias | FIG. | Example z score |
|---|---|---|---|---|---|
| | | TRIM69 | | | -2.94861 |
| | | TRIM21 | | | -2.23631 |
| | | TRIM25 | | | -2.07251 |
| | | TRIM39 | | | -4.44632 |
| | | TRIM8 | | | -2.79096 |
| | | TRIM26 | | | -2.44175 |
| | | TRIM47 | | | -3.35296 |
| | | OASL | | | -2.16662 |
| | | OAS2 | | | -2.52725 |
| | | MX1 | | | -3.4825 |
| 2 | Virus Sensing/ Response | DDX60 | | 1 | -4.23763 |
| | | DDX60L | | 1 | -4.02079 |
| | | DHX58 | LGP2 | 1 | -4.4015 |
| | | DDX58 | RIG-I | 1 | -1.99326 |
| | | ISG15 | | 1 | -2.02978 |
| | | IFIH1 | MDA5 | 1 | -5.37774 |
| | | CD14 | | 2 | -2.37903 |
| | | LBP | | 2 | -2.22118 |
| | | TLR4 | | 2 | -2.00005 |
| | | MYD88 | | 2 | -3.70288 |
| | | TOLLIP | | 2 | -2.48444 |
| | | TLR3 | | 2 | -2.80247 |
| | | TLR5 | | 2 | -3.1459 |
| | | TLR6 | | 2 | -2.40158 |
| | | TLR9 | | 2 | -2.65841 |
| | | TICAM1 | TRIF | 2 | -3.4983 |
| | | IRF7 | | 2 | -1.93673 |
| | | IRF5 | | 2 | -1.71337 |
| | | MAPK11 | p38 | 1, 2 | -3.77409 |
| | | MAPK12 | p38 | 1, 2 | -2.3626 |
| | | MAPK8 | JNK | 1, 2 | -3.43472 |
| | | RIPK1 | RIP1 | 1, 2 | -2.7969 |
| | | IKBKG | IKKy/NEMO | 1, 2 | -2.224 |
| | | NFKBIA | IkB | 1, 2 | -2.33147 |
| 3 | IFN signaling | IFNAR1 | | 3 | -1.01519 |
| | | IFNAR2 | | 3 | -5.32492 |
| | | IFNGR1 | | 3 | -1.24058 |
| | | IRF1 | | 3 | -3.21018 |
| | | JAK1 | | 3 | -1.15905 |
| | | STAT1 | | 3 | -1.33382 |
| | | STAT2 | | 3 | -1.68887 |
| | | STAT3 | | 3 | -2.93352 |
| | | STAT5A | | 3 | -3.40244 |
| | | IRF9 | | 3 | -4.15445 |
| | | PIK3R2 | PI3K | 3 | -2.5087 |
| | | PIK3CG | PI3K | 3 | -2.34346 |
| | | AKT1 | | 3 | -1.61568 |
| | | AKT2 | | 3 | -1.05491 |
| | | AKT3 | | 3 | -1.76727 |
| | | MTOR | | 3 | -2.19278 |
| 4 | MHC peptide presentation | PSMB8 | immunoproteasome | 4 | -5.21096 |
| | | PSMB9 | immunoproteasome | 4 | -3.67239 |
| | | PSMB10 | immunoproteasome | 4 | -1.64741 |
| | | PSME1 | | 4 | -5.31937 |
| | | PSME2 | | 4 | -4.14217 |
| | | TAP1 | | 4 | -4.85621 |
| | | TAP2 | | 4 | -7.41988 |
| | | TAPBP | | 4 | -5.4146 |
| | | TAPBPL | | 4 | -2.53269 |
| | | ERAP1 | | 4 | -2.54984 |
| | | ERAP2 | | 4 | -2.42703 |
| | | CALR | Calreticulin | 4 | -2.8149 |
| | | PDIA3 | ERp57 | 4 | -2.60756 |
| | | HLA-A | MHC class I | 4 | -2.57077 |
| | | HLA-B | MHC class I | 4 | -2.19049 |
| | | HLA-C | MHC class I | 4 | -2.26723 |
| | | BTN3A1 | MHC I associated | 4 | -4.12156 |
| | | BTN3A2 | MHC I associated | 4 | -2.52546 |
| | | BTN3A3 | MHC I associated | 4 | -3.36823 |
| | | B2M | | 4 | -3.043 |

TABLE 2

| Functional Group | Gene | Standardized Expression |
|---|---|---|
| Antiviral (Gene Set 5) | MX1 | −2.48722 |
| | MX2 | −1.86233 |
| | OAS2 | −1.93936 |
| | OASL | −1.7635 |
| | APOBEC3G | −1.97365 |
| | ISG15 | −1.60323 |
| | IFITM3 | −2.47202 |
| | BST2 | −2.6742 |
| | RSAD2 | −2.39164 |
| | IFIT1 | −2.72282 |
| | IFIT2 | −2.35249 |
| | IFIT3 | −2.88401 |
| | IFIT5 | −3.15128 |
| | TRIM25 | −1.81487 |
| | IRF1 | −2.33806 |
| | IRF7 | −1.72574 |
| | IFIH1 | −2.99414 |
| | GBP1 | −2.25249 |
| | GBP2 | −1.54042 |
| | IRF2 | −2.4907 |
| | MAP3K14 | −2.29295 |
| | MOV10 | −2.92639 |
| | RTP4 | −2.06482 |
| Sensing & Signaling (Gene Set 6) | DDX60 | −2.69068 |
| | NFKBIA | −1.8442 |
| | MAPK8 | −2.49321 |
| | MAPK11 | −2.57476 |
| | MAPK12 | −1.97995 |
| | TRAF3 | −1.60033 |
| | DHX58 | −2.87239 |
| | IKBKG | −1.90225 |
| | RIPK1 | −2.24669 |
| | AKT3 | −1.54903 |
| | TAB1 | −2.52914 |
| | TICAM1 | −2.50632 |
| | PIK3R5 | −1.62157 |
| | IFNAR2 | −2.83401 |
| | TICAM2 | −1.54619 |
| | IRF5 | −1.59149 |
| | MYD88 | −2.60928 |
| | PIK3CG | −1.73839 |
| | TLR9 | −2.08964 |
| | TOLLIP | −1.98898 |
| | TLR3 | −2.25984 |
| | TLR4 | −1.51061 |
| | TLR5 | −2.26465 |
| | PIK3R3 | −1.51415 |
| | CD14 | −1.85251 |
| | CASP1 | −2.10785 |
| | STAM2 | −1.73074 |
| | IRF9 | −2.65065 |
| | FHL1 | −1.54226 |
| | MTOR | −1.71734 |
| | STAT2 | −1.50664 |
| | STAT3 | −2.13981 |
| | STAT5A | −2.41269 |
| Antigen Processing & Presentation (Gene Set 7) | PDIA3 | −2.04376 |
| | HLA-A | −2.05677 |
| | HLA-B | −1.74034 |
| | HLA-C | −1.78674 |
| | HLA-E | −2.33325 |
| | HLA-F | −2.14848 |
| | B2M | −2.21826 |
| | PSME1 | −2.83945 |
| | PSME2 | −2.65726 |
| | TAP1 | −2.81875 |
| | TAP2 | −3.14581 |
| | TAPBP | −2.88101 |
| | CALR | −2.15899 |
| | PSMB8 | −2.80432 |
| | PSMB9 | −2.47029 |
| | ERAP1 | −2.02863 |
| | ERAP2 | −2.05253 |
| | TAPBPL | −1.96713 |

Figure 2:
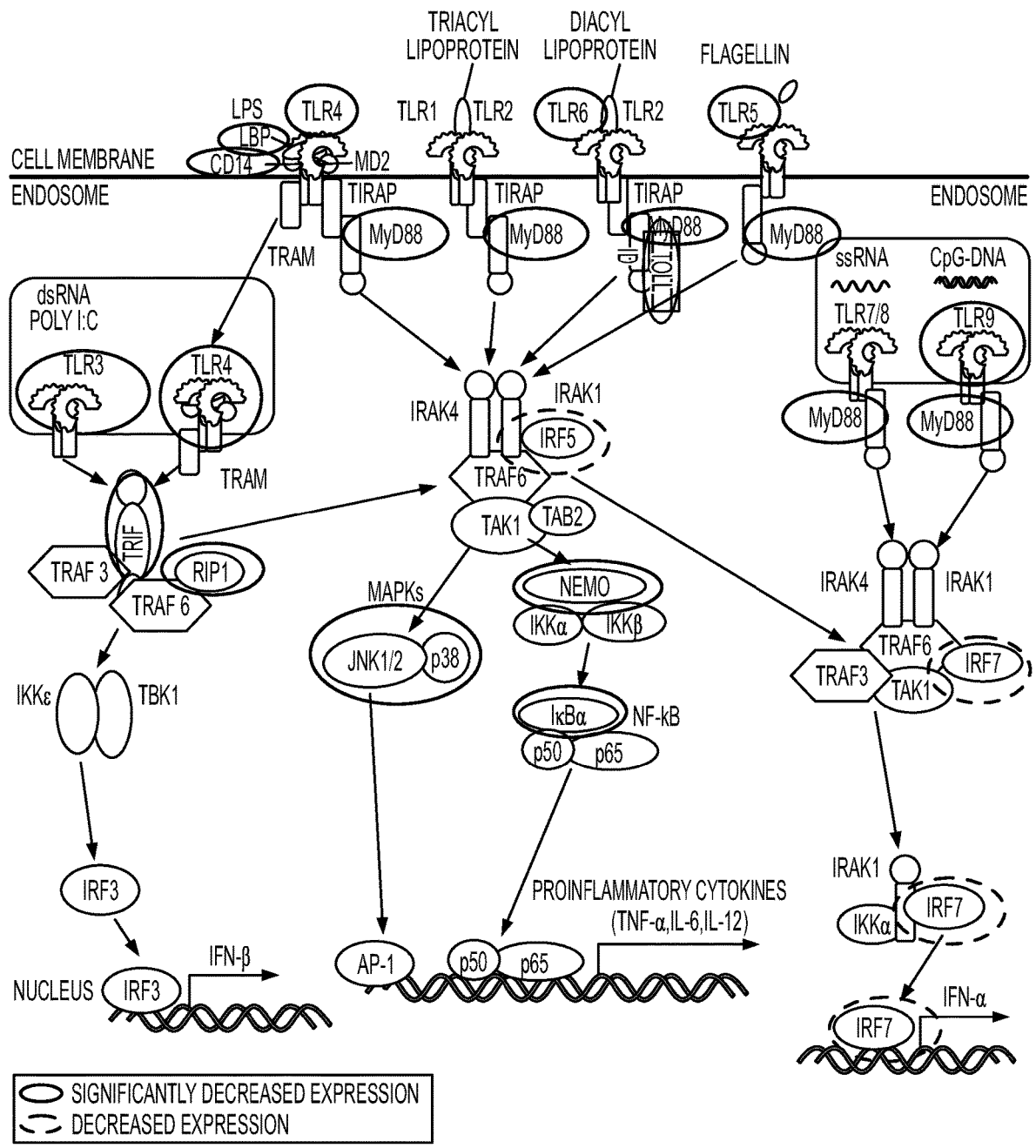
FIG. 2 is a diagram of a molecular Toll-like receptor (TLR) signaling pathway involved in antiviral responses. Virus is detected by transmembrane TLR proteins, which initiate a signaling cascade through cytoplasmic adapter proteins. The activated signaling pathways stimulate production of anti-viral genes including IFN and inflammatory cytokines. Solid black ovals indicate proteins identified to have significantly decreased expression in patient 12, relative to the other 11 patients of the cohort. Dashed black ovals indicate proteins essential to the pathway with decreased expression relative to the cohort.
Figure 3:
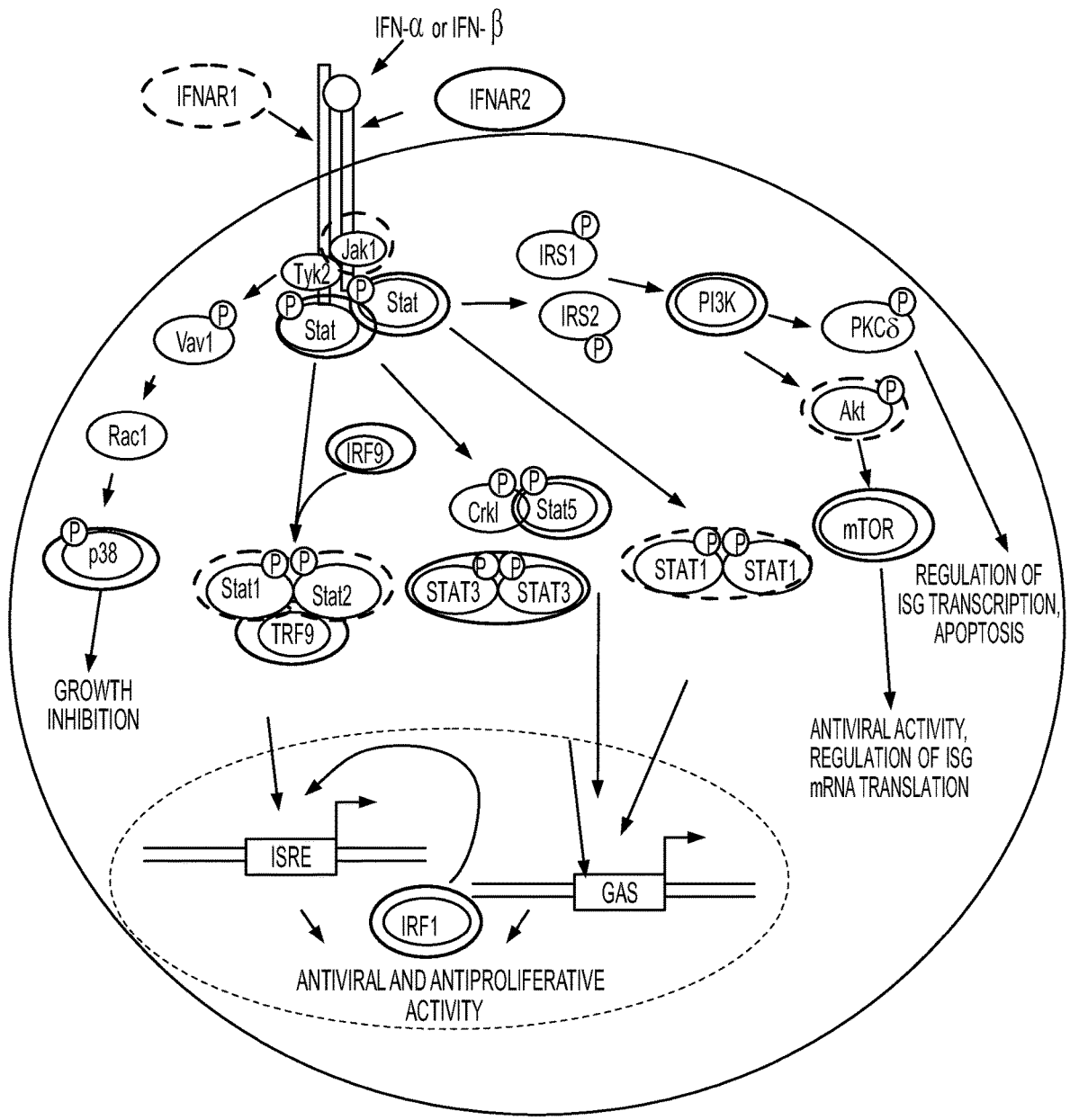
FIG. 3 is a diagram of a cellular antiviral response mediated by sensing and responding to interferon (IFN). The IFN produced from cells sensing viral infection extracellularly signals surrounding cells of infection, inducing and anti-viral cellular state. IFN is detected by transmembrane receptors that interact with JAK and Tyk adaptor proteins, which initiate STAT signaling cascades that turn on ISRE and GAS genes, which in turn generate an anti-viral cellular state. Solid black ovals indicate proteins identified to have significantly decreased expression in patient 12, relative to the other 11 patients of the cohort. Dashed black ovals indicate proteins essential to the pathway with decreased expression relative to the cohort.
Figure 4:
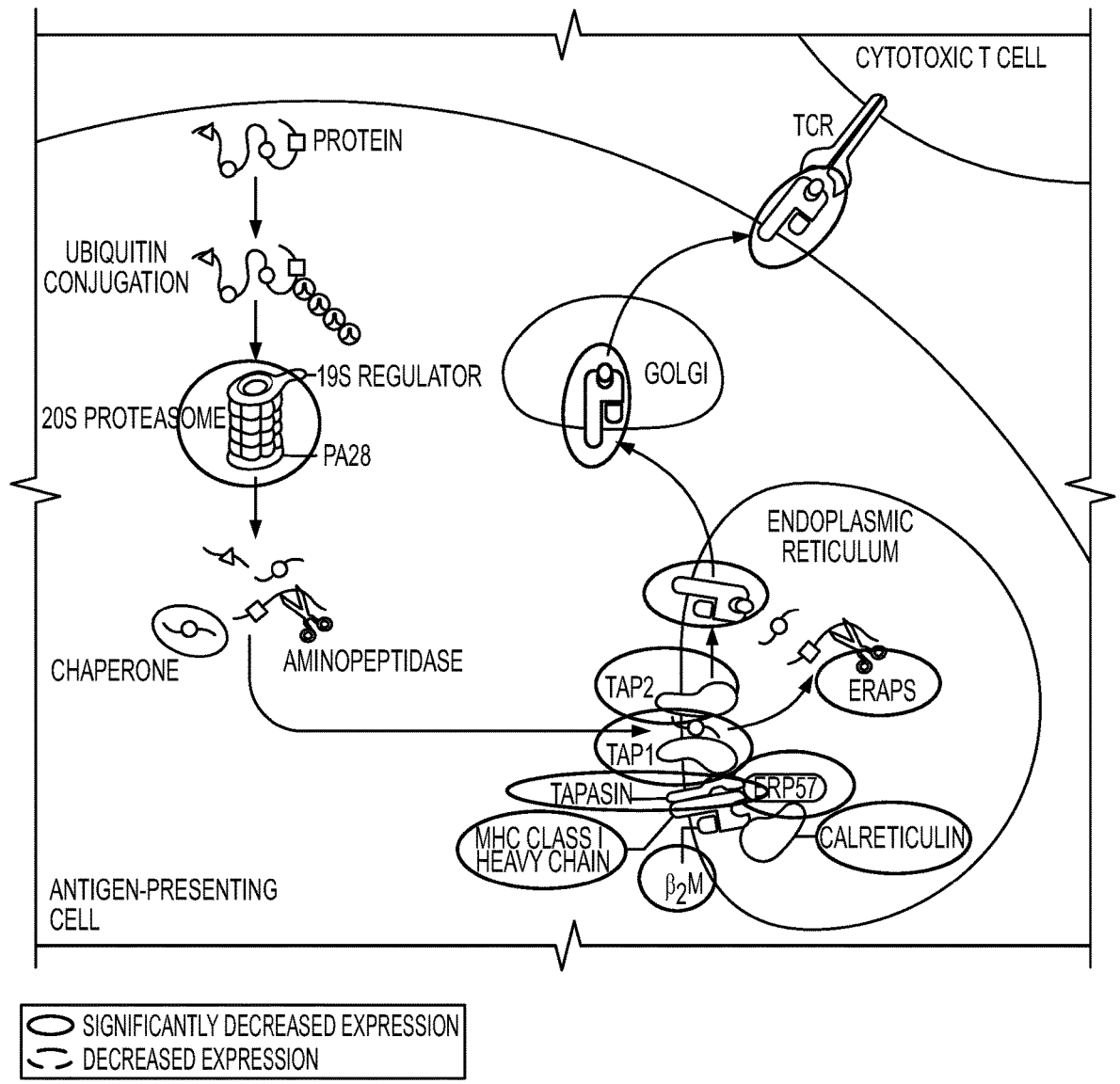
FIG. 4 is a diagram of a virus induced innate immune response involving processing of viral proteins by the immunoproteasome. The cleaved viral peptides are transported to the ER, where they are loaded into class I MHC molecules. Class I MHC molecules loaded with viral antigens are then shuttled to the cellular surface to present the viral antigen to cytotoxic T cells to induce an antiviral immune response.
Figure 5:
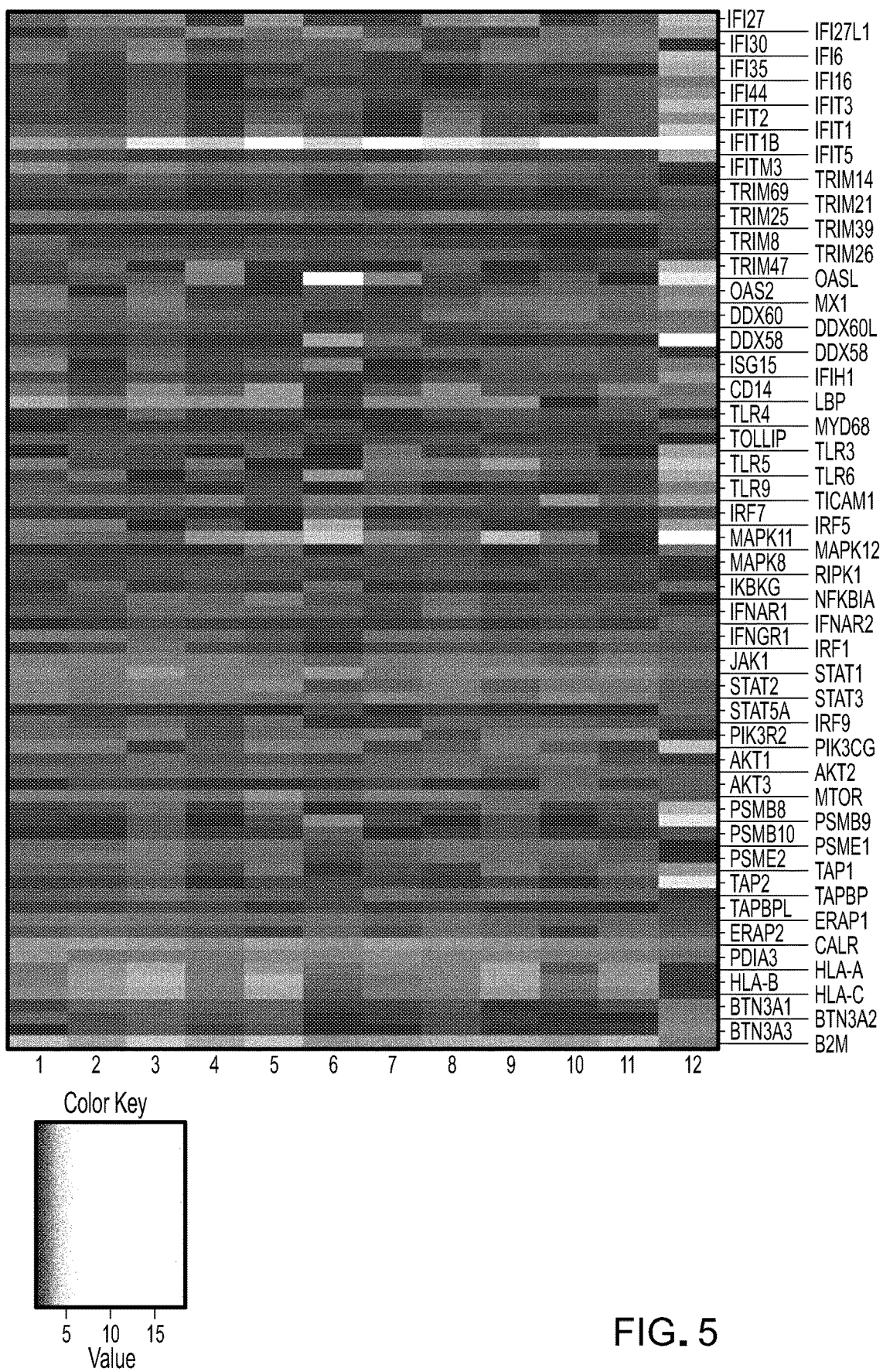
FIG. 5 is a heat map of normalized antiviral gene expression. Genes involved in an antiviral tumor state identify a genetic signature associated with robust viral replication within a tumor of patient 12, relative to patients 1-11 in which virus replication was not detected. Normalized gene expression was determined from RNAseq raw gene counts normalized using DESeq (Love et al., *Genome Biology*, 15:550 (2014)).
Figure 6:
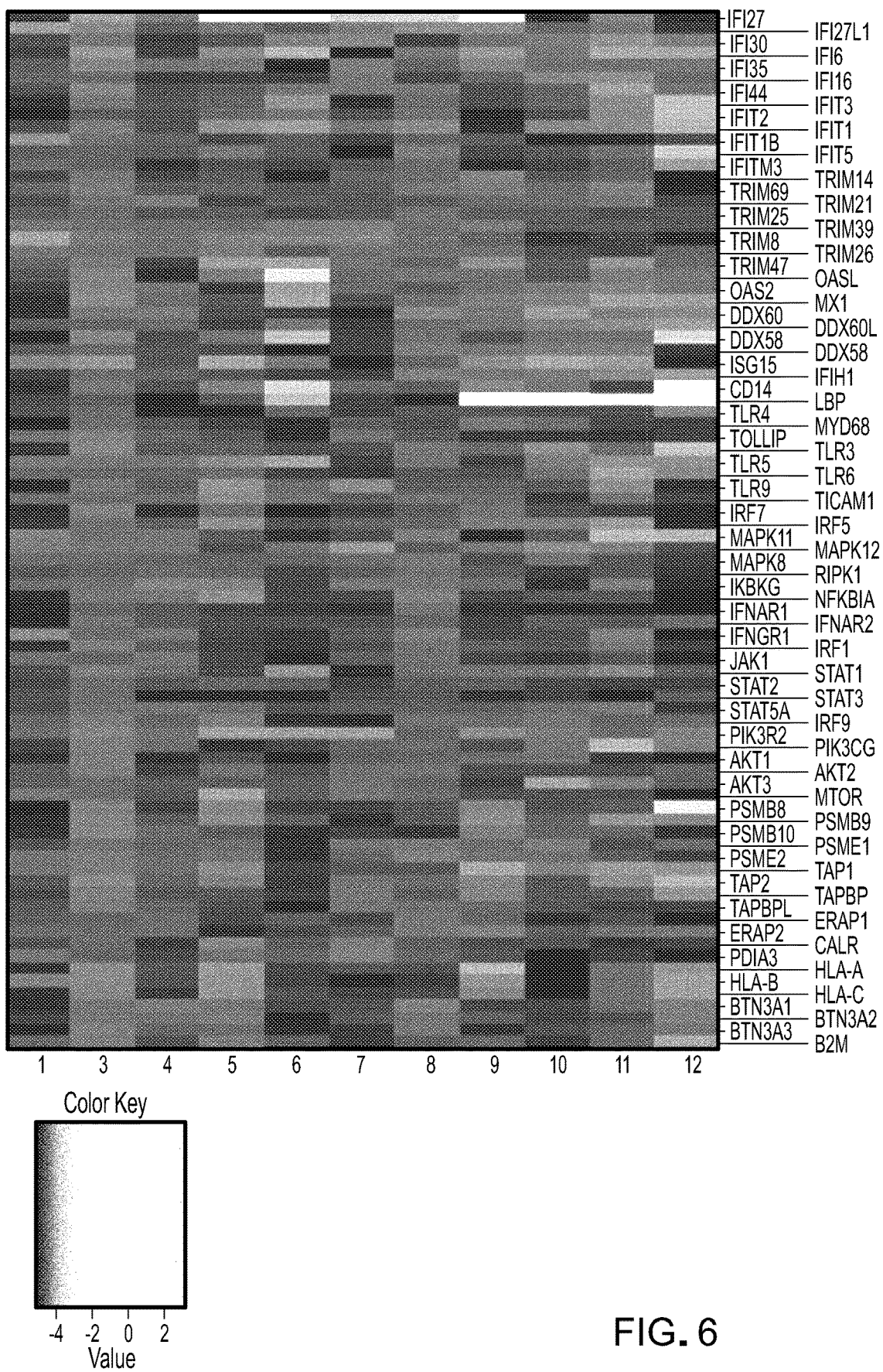
FIG. 6 is a heat map of differentially expressed antiviral genes. Differential gene expression in liver tumors relative to normal liver tissue in genes involved in an antiviral tumor state identify a genetic signature associated with robust viral replication within a tumor of patient 12, relative to patients 1-11 in which virus replication was not detected. Normalized differential gene expression was determined from RNAseq raw gene counts normalized using DESeq by subtracting the natural log of expression levels in normal tissue from the natural log of expression levels in tumor. A negative value indicates expression in the tumor is lower than that observed in normal tissue.
Figure 7:
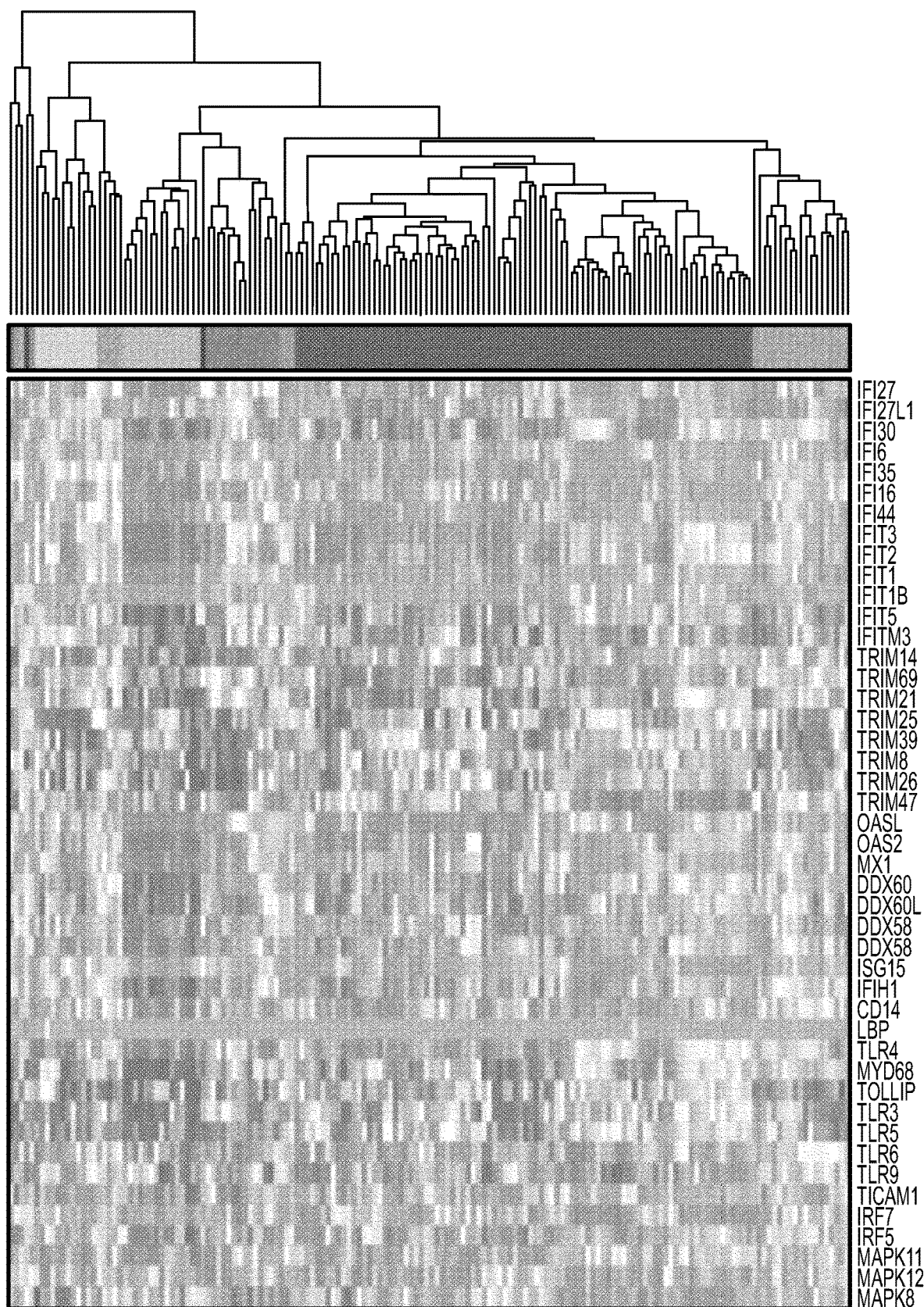
FIG. 7 is a heat map of relative antiviral gene expression in a cohort of colorectal cancer patients collected in The Cancer Genome Atlas (TCGA) database. The heat map colors indicate the magnitude of z-score, which relates the individual gene expression to the median gene expression level. The lower z-score indicates lower gene expression relative to the median expression level. The cohort was separated into clusters of patients determined by the similarity of gene expression patterns using the heatmap.2 clustering function from R package gplots (https://cran.r-project.org/web/packages/gplots/gplots.pdf). The bracket below indicates clusters that visually appear to have decreased expression of the antiviral signature genes relative to the rest of the cohort.
Figure 7:
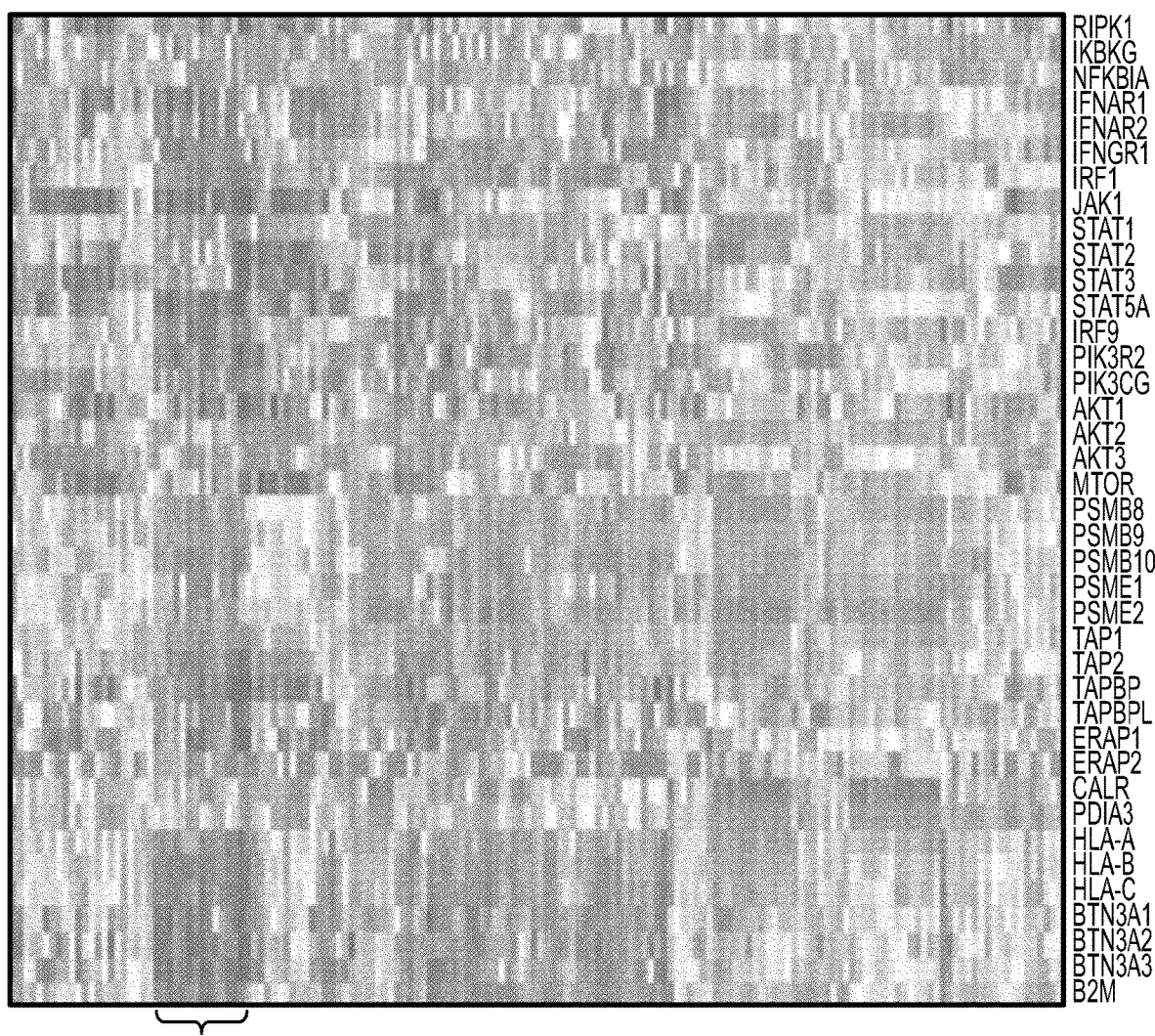
Figure 8:
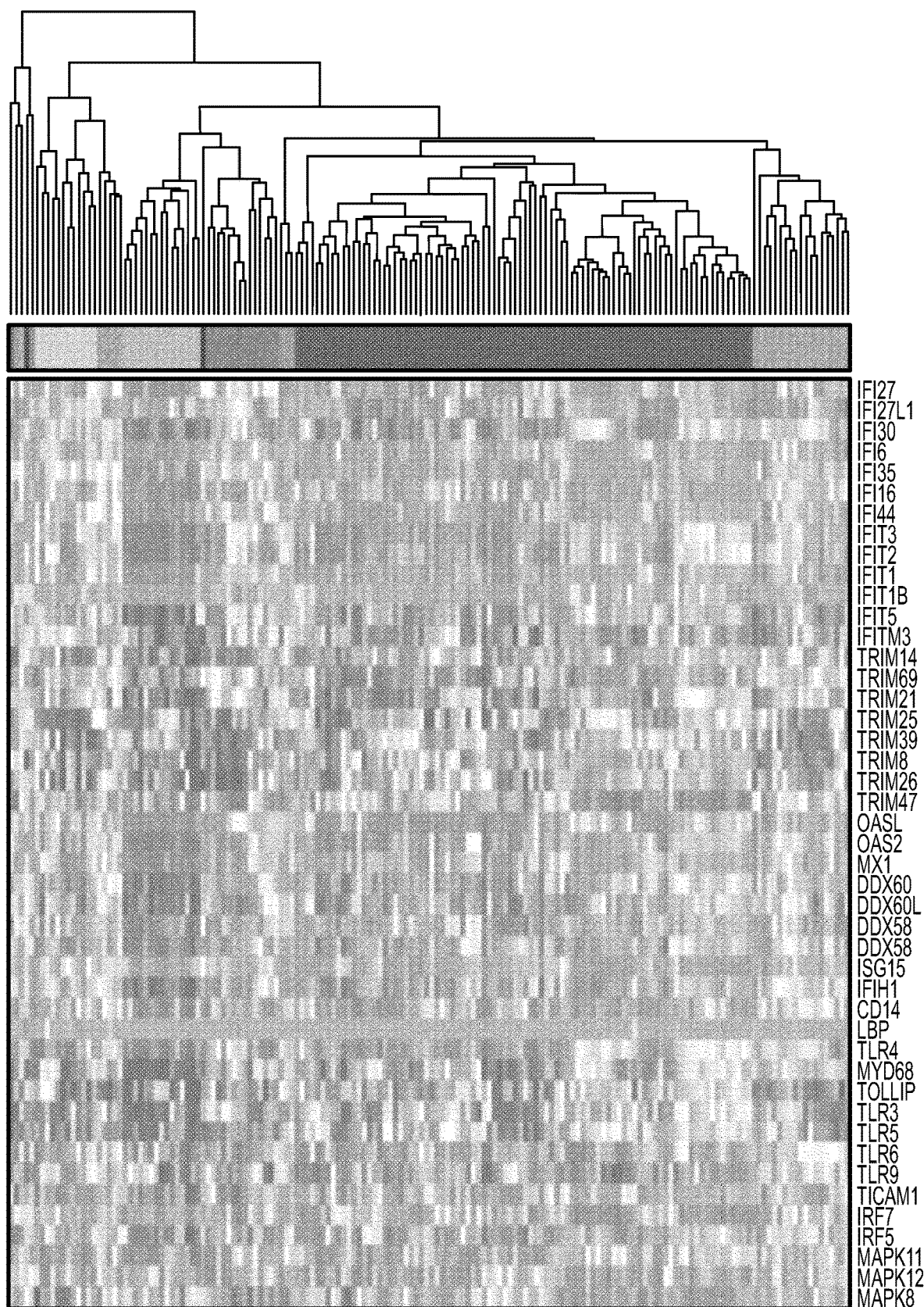
FIG. 8 is a heat map of relative antiviral gene expression in a cohort of lung adenocarcinoma cancer patients collected in the TCGA database. The heat map colors indicate the magnitude of z-score, which relates the individual gene expression to the median gene expression level. The lower z-score indicates lower gene expression relative to the median expression level. The cohort was separated into clusters of patients with similar gene expression patterns using the heatmap.2 clustering function from R package gplots. The bracket below indicates a cluster that appears to have decreased expression of the antiviral signature genes relative to the rest of the cohort.
Figure 8:
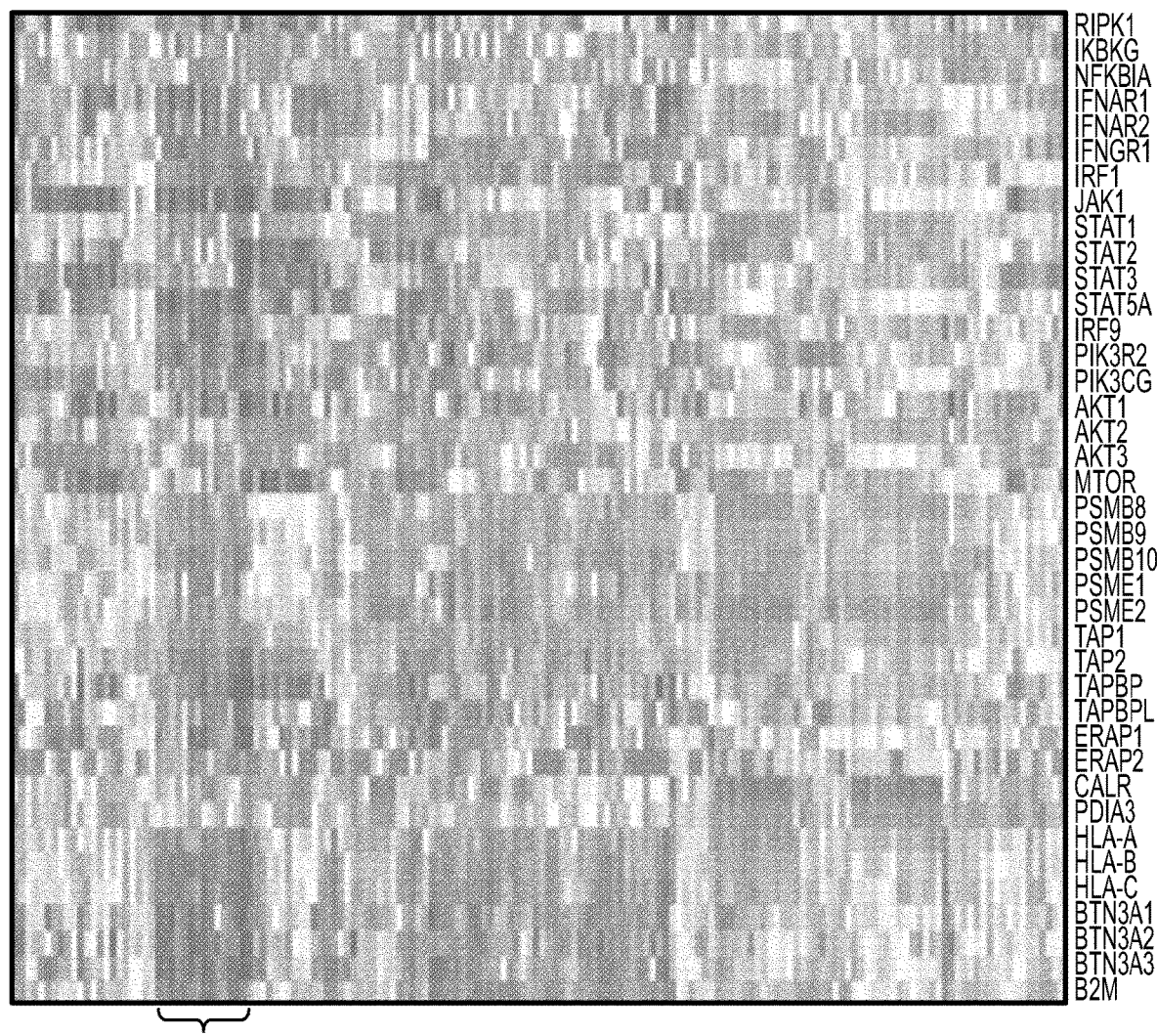

In some cases, the gene sets can relate to four conditions: an antiviral state, viral sensing and signaling (FIGS. 1 and 2), IFN-response (FIG. 3), and peptide processing and presentation (FIG. 4). Each of the genes listed in Table 1 and/or Table 2 can have a relationship to the virotherapy permissive state of the cancer cell. In some cases, the tumor-specific RNA expression of all genes contained within each of the four gene sets of Table 1 (or a virotherapy permissive gene expression signature) or a subset of genes from about 50 percent to about 100 percent (e.g., from about 60 percent to about 100 percent, from about 70 percent to about 100 percent, from about 75 percent to about 100 percent, from about 80 percent to about 100 percent, or from about 90 percent to about 100 percent) of the genes contained within each of the four gene sets of Table 1 (or a virotherapy permissive gene expression signature) can be used and compared to control cell values to determine whether or not the cancer cell has a low expression score for each gene set. In some cases, the tumor-specific RNA expression of all genes contained within each of the three gene sets of Table 2 (or a virotherapy permissive gene expression signature) or a subset of genes from about 50 percent to about 100 percent (e.g., from about 60 percent to about 100 percent, from about 70 percent to about 100 percent, from about 75 percent to about 100 percent, from about 80 percent to about 100 percent, or from about 90 percent to about 100 percent) of the genes contained within each of the three gene sets of Table 2 (or a virotherapy permissive gene expression signature) can be used and compared to control cell values to determine whether or not the cancer cell has a low expression score for each gene set.

In general, regarding Gene Set 1 (and Gene Set 5), when a cell is in an antiviral state, initiated after reception of cytokine signals from neighboring infected cells, a set of genes encoding antiviral proteins can be induced. These proteins serve as the initial line of defense against viral infection and replication. When a cell is not in an antiviral state (has not responded to cytokine signaling), the levels of mRNAs encoding certain antiviral proteins known to inhibit virus life cycles are low. The lack of a baseline antiviral state allows initial viral replication upon therapeutic administration to occur. Cells that are not in an "antiviral state" do not efficiently block oncolytic virus replication.

In general, regarding Gene Set 2 (and Gene Set 6), viral sensing machinery allows a cell to detect infection and activate a constellation of antiviral responses via signaling pathways that can allow the cell to assume an antiviral state. In a normal cell, the viral sensing machinery signals through several intracellular signaling pathways to activate the expression of an array of genes whose encoded products are able to interfere with multiple components of the viral life cycle. After initial treatment, tumor cells in which there is low basal expression of proteins involved in viral sensing and signal transduction do not efficiently sense that they have been infected by an oncolytic virus and therefore do not efficiently assume an "antiviral state".

In general, regarding Gene Set 3 (and Gene Set 6), one of the proteins typically secreted by virus-infected cells is interferon-β. This is particularly so for patients treated with VSV-IFNβ because the genome of this virus was engineered to drive high level expression of a virus-encoded interferon-β transgene. Typically, interferon-β will bind to receptors of nearby cells and initiate a cascade of intracellular signaling events leading to the expression of IFN-stimulated genes that create an "antiviral state". In tumor cells with low expression of these IFN responsive genes at baseline, the cells are not responsive to IFN signaling and therefore do not efficiently assume an "antiviral state".

In general, regarding Gene Set 4 (and Gene Set 7), an antiviral mechanism of cells to stop the replication and spread of viral infection is cell-mediated immunity. In this process, virus infected cells can process intracellular proteins and present 'non-self' peptides via MHC class I molecules on the cell surface to induce a cytotoxic immune response. When antigenic viral proteins are processed and presented by MHC class I molecules on the surface of tumor cells, cytotoxic T lymphocytes can recognize and kill the infected cell, thereby halting viral progeny production and the spreading of infection. In tumor cells with low expression of proteins involved in the processing of antigenic peptides and class I MHC complexes, the cells are unable to effectively present antiviral antigens to immune cells and therefore do not efficiently induce an innate immune response.

Again, as described herein, the presence of a virotherapy permissive gene expression signature in cancer cells can be used to identify a subset of cancer patients more likely to respond to replicating oncolytic virotherapy and allow for anticipation of rapid tumor lysis. In some cases, a tumor biopsy is obtained, RNA is extracted, and the RNA is tested by, for example, microarray analysis to determine baseline intratumoral normalized RNA expression level of each gene within the four gene sets listed in Table 1 and/or within the three gene sets listed in Table 2 as well as a control housekeeping gene or a control housekeeping gene set. Examples of control housekeeping genes include, without limitation, ACTB, EFlalpha, GAPDH, HRPT1, VCP, and RPL13A. In addition, RNA is extracted from control cells (e.g., a normal tissue or a cell population such as peripheral blood mononuclear cells (PBMCs)) of the same patient, and the RNA is subjected to the same microarray analysis. The relative expression levels of each gene (or a subset of at least about 50 percent of the genes) within each of the four gene sets of Table 1 (and/or within the three gene sets listed in Table 2) and one or more housekeeping genes are determined for the tumor biopsy tissue versus control cells. Using those relative expression levels, a "low" or "not low" expression score can be assigned to each of the four gene sets of Table 1 (and/or each of the three gene sets listed in Table 2). In some cases, the level of a low score can be determined, based on the degree of reduced expression of the genes being assessed for each gene set of Table 1 and/or Table 2, as being "significantly low" when the average gene expression is reduced more than about 2.0 standard deviations or "moderately low" when the average gene expression is reduce by about 1.64 standard deviations to about 2.0 standard deviations.

In some cases, gene expression levels (e.g., RNA expression scores) for the genes being assessed for each gene set of Table 1 (and/or Table 2) can be gene expression values such as raw counts, normalized gene counts, z-scores comparing gene expression relative to a known cohort or expression level, or differential expression of genes relative to normal tissue biopsy.

In some cases, RNA from a mammal's tumor biopsy (e.g., a human's tumor biopsy) and a normal biopsy can be sequenced and aligned, and gene counts can be determined. For example, targeted microarrays or RNAseq can be used to assess expression of signature genes and housekeeping genes. The gene counts can be normalized, and comparison of gene expression levels for each gene can be performed using one of the following five methods.

1) Z-score relative to established mean or median. The mean or median expression level of genes in a population of tumor samples of the same tumor origin can be determined using the same normalization techniques to account for batch effect. The patient's gene expression can then be compared to the mean or median to determine how significant the difference in expression level is using a z score. A z-score is a statistical measure of a measurement's relationship to the mean or median of a population's measurement. A z score can be calculated using the following formula: $z=(x-\mu)/\sigma$, where x is the gene expression level in the patient, $\mu$ is the mean or median gene expression level in the sample population, and a is the standard deviation in gene expression level for the sample population. The gene expression level can be considered significantly low when $z \le -1.96$, and moderately low when $z \le -1.64$.

2) Gene expression relative to a threshold. A threshold gene expression level can be determined, which describes a significant decrease relative to an established normal gene expression level. The established normal level can be determined by consideration of a large population of tumor samples. The threshold can be set by considering the standard deviation of gene expression (e.g., two standard deviations from the mean) or by a predetermined level known to functionally alter cellular activity.

3) Differential expression relative to normal biopsy. The gene expression level for each gene in the tumor sample can be compared to that in the normal biopsy sample. The fold change (FC) relative to normal can be determined for each gene. $FC=x_t/x_n$, where $x_t$ is the gene expression level in the tumor, and $x_n$ is the gene expression level in the normal tissue. The $\log_2$ of the fold change can be used to determine whether the fold change is significant. A $\log_2$ fold change $\le -1$ indicates at least a twofold decrease in expression.

4) Differential expression relative to population mean or median. Similar to "3)", the gene expression levels from the patient's tumor can be compared to the average expression level of a population of tumor samples from the same tumor type or an established average population level as, for example, described in "1)".

5) Differential expression relative to housekeeping genes. Similar to the description in "3)", the gene expression levels from the patient's tumor can be compared to the average expression level of a collection of housekeeping genes quantified in the patient's tumor sample. Housekeeping genes are genes known to have steady expression levels regardless of treatment or cellular state and can serve as a marker for standard expression. The differential expression can be determined for each gene relative to housekeeping genes. Additionally, the average fold change within a population of the same tumor type can be determined to account for deviations in expression from the housekeeping genes that are present for the genes in the gene set. Fold change relative to housekeeping genes or deviation from the gene's average fold change relative to housekeeping can indicate a relevant change in expression level.

Following comparison of gene expression for each gene being evaluated for one of Gene Sets 1-4 (and/or one of Gene Sets 5-7), a score can be assigned to describe the expression status of each of the four gene sets (and/or each of the three gene sets of Table 2) and therefore the activity of the corresponding antiviral function. For example, if most (e.g., 60%, 70%, 80%, 90%, or more) of the genes within a gene set being evaluated (e.g., six, seven, eight, nine, or ten out of ten if ten are selected from Gene Set 1) are determined to have low expression, than that gene set (e.g., Gene Set 1) can be identified as having low expression.

In some cases, the number of gene sets that have low expression can be used to determine how to treat the cancer. For example, the treatment options described in Table 3 can be used to treat cancer. Examples of sensing inhibitors include, without limitation, NFkB inhibitors such as bortezomib, carfilzomib, and lestauritinib. Examples of IFN inhibitors include, without limitation, JAK/STAT pathway inhibitors such as tofacitinib, ruxolitinib, and baricitinib.

TABLE 3

| Signature Expression Score | Treatment Option |
|---|---|
| Significantly Low in all four gene sets of Table 1 | Treat with oncolytic virus(es) at single low to moderate dose (IV or intratumoral administration), increase monitoring for tumor lysis |
| Moderately Low in all four gene sets of Table 1 | Treat with oncolytic virus(es) at low initial dose (IV or intratumoral administration), monitor, follow up with possible higher dose (intratumoral administration) |
| Gene Sets 1, 2, 3 low (4 is not low) | Single high dose oncolytic virus(es) (intratumoral administration) |
| Gene Sets 1, 3, 4 low (2 is not low) | Low dose oncolytic virus(es) together with sensing inhibitors |
| Gene Sets 1, 2, 4 low (3 is not low) | Low dose oncolytic virus(es) together with IFN inhibitor |
| Gene Sets 2, 3, 4 low (1 is not low) | Single high dose oncolytic virus(es) (intratumoral administration) |
| All four gene sets of Table 1 not low | Repeat high dose oncolytic virus(es) (intratumoral administration) as immunotherapy with or without checkpoint inhibitors |
| Significantly Low in all gene sets of Table 2 | Treat with oncolytic virus(es) at single low to moderate dose (IV or intratumoral administration), increase monitoring for tumor lysis |
| Moderately Low in all gene sets of Table 2 | Treat with oncolytic virus(es) at low initial dose (IV or intratumoral administration), monitor, follow up with possible higher dose (intratumoral administration) |
| Gene Sets 5 and 6 low (7 is not low) | Single high dose oncolytic virus(es) (intratumoral administration) |
| Gene Sets 5 and 7 low (6 is not low) | Low dose oncolytic virus(es) together with sensing inhibitors and/or IFN inhibitors |
| Gene Sets 6 and 7 low (5 is not low) | Single high dose oncolytic virus(es) (intratumoral administration) |
| All gene sets of Table 2 not low | Repeat high dose oncolytic virus(es) (intratumoral administration) as immunotherapy with or without checkpoint inhibitors |

If all four gene sets of Table 1 (or all three gene sets of Table 2) of the virotherapy permissive gene expression signature have significantly low expression scores, then the mammal can be identified as having cancer cells with the virotherapy permissive gene expression signature and as being likely to experience extensive intratumoral/systemic spread of a therapeutically administered oncolytic virus. In such cases, one or more oncolytic viruses can be administered to the identified mammal as the sole active anticancer agent or in combination with other anticancer agents. For example, a mammal (e.g., a human) identified as having cancer cells with all four gene sets of the virotherapy permissive gene expression signature having significantly low expression scores can be administered (e.g., intravenously or intratumorally) a single low (e.g., from about $1 \times 10^6$ $TCID_{50}$ to about $1 \times 10^8$ $TCID_{50}$) or moderate (e.g., from about $1 \times 10^8$ $TCID_{50}$ to about $1 \times 10^9$ $TCID_{50}$) dose of an oncolytic virus. In this case, the mammal can be monitored closely (e.g., every two hours for about seven days) for tumor lysis and treated, if needed, with intravenous fluids, rasburicase, and/or anticoagulants to minimize systemic toxicities caused by a tumor lysis syndrome.

If all four gene sets of Table 1 (or all three gene sets of Table 2) of the virotherapy permissive gene expression signature have moderately low expression scores, then the mammal can be identified as having cancer cells with the virotherapy permissive gene expression signature and as being likely to experience extensive intratumoral/systemic spread of a therapeutically administered oncolytic virus. In such cases, one or more oncolytic viruses can be administered to the identified mammal as the sole active anticancer agent or in combination with other anticancer agents. For example, a mammal (e.g., a human) identified as having cancer cells with all four gene sets of the virotherapy permissive gene expression signature having moderately low expression scores can be administered (e.g., intravenously or intratumorally) a single low (e.g., from about $1 \times 10^6$ $TCID_{50}$ to about $1 \times 10^8 TCID_{50}$) initial dose of an oncolytic virus. In this case, the mammal can be monitored closely (e.g., every two hours for about seven days) for tumor lysis and treated, if needed, with intravenous fluids, rasburicase, and/or anticoagulants to minimize systemic toxicities caused by a tumor lysis syndrome. The mammal also can be administered repeated follow up doses higher than the initial dose to further reduce the number of cancer cells.

If all four gene sets of Table 1 (or all three gene sets of Table 2) of the virotherapy permissive gene expression signature have do not have low expression scores, then the mammal can be identified as having cancer cells lacking a virotherapy permissive gene expression signature and as being unlikely to experience extensive intratumoral/systemic spread of a therapeutically administered oncolytic virus. In such cases, one or more oncolytic viruses can be administered intratumorally to the identified mammal repeatedly (e.g., every two to four weeks) at a high dose (e.g., greater than about $1 \times 10^9$ $TCID_{50}$ per injection) as immunotherapy alone or in combination with one or more checkpoint inhibitors. Examples of checkpoint inhibitors include, without limitation, anti-PD1 antibodies, anti-PD-L1 antibodies, and anti-CTLA4 antibodies. For example, a mammal (e.g., a human) identified as having cancer cells with all four gene sets of the virotherapy permissive gene expression signature lacking low expression scores can be administered (e.g., intratumorally) repeated high doses (e.g., greater than about $1 \times 10^9$ $TCID_{50}$ per injection) of an oncolytic virus.

The invention will be further described in the following examples, which do not limit the scope of the invention described in the claims.

EXAMPLES

Example 1—Analysis of Cancer Cells Responsive to Oncolytic Virus Treatment

The RNAseq data from tumor and normal liver biopsies obtained at baseline as well as days 2 and 8 post virus administration from 12 patients with primary or metastatic liver cancer were analyzed. The 12 patients were treated by intratumoral inoculation of a low dose (dose escalation trial in which patients were treated with a single dose ranging from $1 \times 10^5$ to $2 \times 10^7$ $TCID_{50}$) of VSV-hIFNβ, an oncolytic vesicular stomatitis virus that was engineered to express a human interferon-β cDNA (Naik and Russell, Expert Opin. Biol. Ther., 9:1163-1176 (2009)). Of the 12 treated patients, only one patient (patient 12) experienced extensive intratumoral and viremic virus spread with associated tumor lysis syndrome. In the remaining 11 patients, the infection was rapidly contained.

Comparing the RNAseq data from normal liver and baseline tumor biopsy material of all 12 virus treated patients, the tumor tissue of patient 12 was identified as uniquely expressing (i) low levels of mRNAs encoding certain antiviral proteins known to inhibit RNA virus life cycles, (ii) low levels of mRNAs encoding certain proteins known to be involved in early detection, signaling, and rapid response to RNA virus infection, (iii) low levels of mRNAs encoding certain proteins known to be involved in the induction of interferon-responsive genes after exposure to interferon-β, and (iv) low levels of a combination of proteins known to be involved in antigen processing and presentation in MEW Class 1 molecules.

Analysis of these altered gene expression patterns revealed four Gene Sets that exhibit lower expression levels in tumor tissue (e.g., a tumor biopsy) from patient 12 relative to normal liver tissue and relative to tumor biopsies from patients 1 to 11 (Table 1). Briefly, a gene signature (e.g., a virotherapy permissive gene expression signature) for robust viral replication within tumors involved four groups including genes involved in the antiviral cellular state, antiviral sensing and signaling, viral processing, and antigen presentation. Gene alias/protein names, z-score, signature group, and corresponding figure for pathway illustration are listed.

The gene signature was applied to the normalized gene expression from the biopsies of the 12 primary or metastatic liver cancer patients treated with intratumoral VSV-hIFNβ. FIG. 5 shows the normalized gene expression levels of the antiviral signature genes in the 12 patients. Patient 12, in which viral replication was observed, exhibited decreased expression of these genes relative to the remaining patients. The z-scores indicating the significance of this decreased expression are listed in Table 1. The differential expression of the gene signature also was determined for these patients. The log normalized gene expression for all antiviral signature genes was compared to the log normalized gene expression in the normal liver tissue biopsy from the same patient. A negative differential expression indicates that expression was lower in the tumor biopsy than in the normal liver biopsy. FIG. 6 shows that the differential expression of the signature genes was lower than that of the remaining patients.

The gene signature also was applied to the normalized gene expression of two separate cancer populations publicly available through The Cancer Genome Atlas (TCGA). For each patient, the RPKM value (reads per kilobase of transcript per million mapped reads) for each gene within the signature was compared to the median RPKM value for that gene within the population. The z score was determined to describe gene expression relative to the median. A negative z score indicated gene expression was less than the median expression level for that gene. In a colorectal cancer cohort, the gene signature identified about 20% of the colorectal cancer patients as having decreased expression of the signature genes (FIG. 7). In a lung adenocarcinoma cohort, the gene signature identified about 10% of the lung adenocarcinoma patients as having decreased expression of the signature genes (FIG. 8).

These results demonstrate that reduced levels of expression of the genes of Gene Sets 1-4 by tumor cells can be used to determine whether or not the tumor deposits in a given cancer patient are likely to support or resist the propagation of an oncolytic virus prior to treatment.

Example 2—Transcriptomic Analysis of Host Innate Immune Responses to VSV-hIFNβ Virotherapy in Primary and Metastatic Liver Cancer Patients Clinical Trial and Tissue Sample Collection A phase I clinical trial to evaluate safety of intratumoral (IT) VSV-hIFNβ administration in primary liver cancer or cancer metastatic to the liver was initiated. In short, the trial was a dose escalation study with starting dose of $1\times10^5$ 50% tissue culture infective dose ($TCID_{50}$), following a standard 3×3 dose escalation scheme. The VSV-hIFNβ was generated, and a total of 12 patients were enrolled and treated on the clinical trial treated at doses $1\times10^5$ (N=3), $5\times10^5$ (N=3), $3\times10^6$ (N=4), $1.8\times10^7$ (N=2) $TCID_{50}$. Patients enrolled included primary hepatocellular cancer (HCC, patient 1-8), cholangiocarcinoma (CCA, patient 10), prostate cancer with liver metastases (patient 11), and colorectal cancer with liver metastases (patient 9 and patient 12). All cancer types were confirmed by pathology report. VSV-hIFNβ was injected IT using radiographic guidance as a single dose into a single lesion. Biopsies of injected tumor and uninvolved normal liver tissue were obtained prior to injection. Tumor biopsies were also collected D2 and D8 following injection. All tissue biopsies were preserved in RNAlater and frozen at −80° C. until use.

RNA Extraction and RNA Sequencing

Total RNA was extracted from frozen tissue samples using RNeasy Plus Universal Kit according to the instructions of the manufacturer (QIAGEN, Valencia, CA). All extracted RNAs were subjected to on-column DNase treatment (QIAGEN), quantification by Agilent quality control (QC) test, and integrity testing using the Agilent 2100 bioanalyzer. Library preparation with Illumina TruSeq Stranded Total RNA sample Preparation kits was performed using 200 ng of total RNA (20 ng/μL). Subsequent cluster generation and DNA sequencing was performed on Illumina HiSeq2500HO sequencer with 101 base paired-end read by the Mayo Clinic Genome Sequencing core.

RNA Sequencing Data Processing

RNA sequencing alignment and quantification was performed using FASTQ files on the MAP-Rseq pipeline, a comprehensive computational workflow developed at the Mayo Clinic for RNA-Seq data analysis. The workflow includes several steps: (1) Tag quality control, (2) Tag alignment: paired-end reads aligned against the human genome (version hg19) with a total of 57773 gene features annotated by Ensembl gene annotation for hg19 obtained, (3) Gene filtration: remove genes with low abundance and genes with less than 2 samples satisfying CPM (count-per-million)>1. (4) Gene count normalization: the log 2-transformed normalized expression value of each gene was calculated using a robust TMM normalization method implemented in the edgeR package in R. Differentially expressed genes were identified using a log 2 ratio with log 2 ratio=1.0 used as significance cutoff. Gene function, pathway and network analyses were done using Ingenuity Pathways Analysis (IPA) software package (QIAGEN, Valencia, CA).

RNAseq of tumor biopsies resulted in high coverage and mapping of RNA. For each tumor biopsy RNA sample, 100-200 million (M) total RNA reads were obtained, of which 87-166M (75.4-91.6%) reads were mapped to the human reference genome with an average base coverage of 1,391 at D2 and 84,578 at D8 post administration. 29,627 expressed genes passed low abundance thresholds and were used in downstream analysis.

Statistical Comparisons

Statistical analyses and plotting were performed in R version 3.2.0, using RStudio. 36 MA plots and heatmaps were created using custom scripts in R package ‘gplots’ version 3.0.1. Fischer’s exact test was used for comparison of nominal variable (inclusion in gene set and inclusion in significant expression) distribution. The z-score statistic was used for standardization of normalized expression values with respect to the population mean/median. To identify the featured genes in the expression profile of the patient with viral replication (patient 12), a robust Z-test method was performed for each gene by comparing the expression distribution of the population baseline (patient 1-11) to the expression in the patient and the corresponding p-value was obtained. Adjusted p-values (false discovery rate, FDR) were also calculated from the z-score based on a two-sided (two-tailed) test to control the rate of false positives (type I error rate) caused by performing multiple tests for all expressed genes. Genes with significantly different expression in the patient with replication were identified as those with an adjusted p-value (FDR)<0.05.

MA plots were generated using regularized log transformed counts. Significant upregulation of gene expression in the tumor relative to normal tissue was identified as log 2 (fold change) (FC)>1 and significant downregulation of gene expression in the tumor relative to normal tissue was identified as log 2FC<−1 with p-value (FDR adjusted)<0.05.

Results

Trial Results Identify Patient 12 as Outlier for Viral Replication

A first-in-human phase I clinical trial with single dose IT administration of VSV-hIFNβ for treatment of refractory primary or metastatic liver cancer was initiated to determine dosing and safety associated with VSV-hIFNβ. Twelve patients were treated by single dose IT VSV-hIFNβ injection into a single lesion at escalating doses as described herein. Tumor and surrounding normal liver tissue were biopsied, and serum was collected prior to, and at D2 and D8 post virus administration. Of the 12 treated patients, one (patient 12) experienced extensive intratumoral and viremic virus spread with associated tumor lysis syndrome while infection was rapidly contained in the remaining 11 patients. This created a unique opportunity to investigate baseline differences in tumors that may determine viral permissivity.

Of the patients treated with IT VSV-hIFNβ, patient 12 was an extreme outlier for virus replication (FIGS. 10A-E). The intratumoral and viremic virus spread exclusive to patient 12 was evidenced by the distribution of viral genomes monitored using qRT-PCR of VSV-N in tumor tissue and blood. Results revealed increasing levels of VSV-N mRNA copies detected D2 and D8 following virus administration in the tumor of patient 12 with parallel increases of VSV-N mRNA in blood and uninfected liver tissue demonstrating viremic spread. VSV-N copies were not detectable in RNA from tumor tissue or blood of patients 1-11 following virus administration.

Figure 10A:
FIGS. 10A-E. Intratumoral virus replication, viremia, and tumor necrosis detected exclusively in patient #12 treated with oncolytic VSV-IFNβ. (A) VSV-hIFNβ genome. (B) VSV-N copies in the tumor and blood of patient 12 increased D2 and D8 following administration, while VSV-N was undetectable after administration in patients 1-11. (C) Viral genes were detected using RNAseq in both D2 and D8 tumor biopsies. Attenuated gene expression can be seen (especially at D2) correlating with VSV replication. (D) IFNβ was detectable in the serum of pt 12 through D13 post administration. (E) Histology of tumor biopsy from patient 12 at baseline, D2, and D8 after administration revealed complete necrosis of tumor tissue by D8.
Figure 10B:
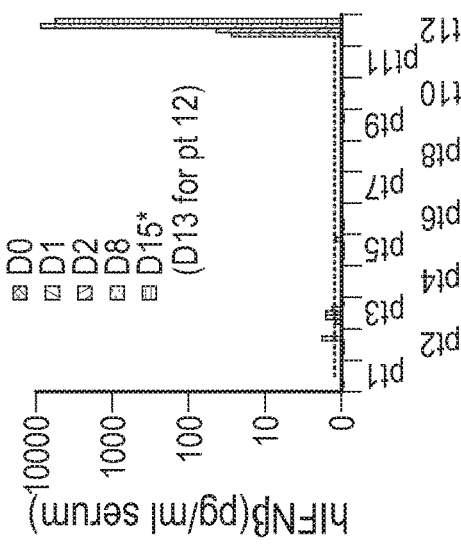
Figure 10C:
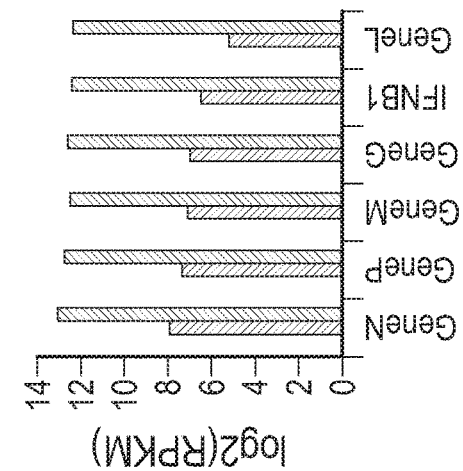
Figure 10D:
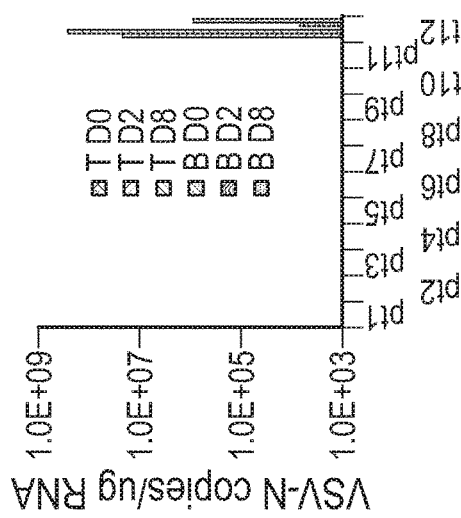
Figure 10E:
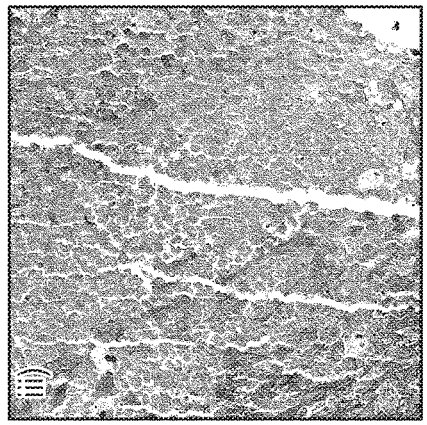
Figure 10E:
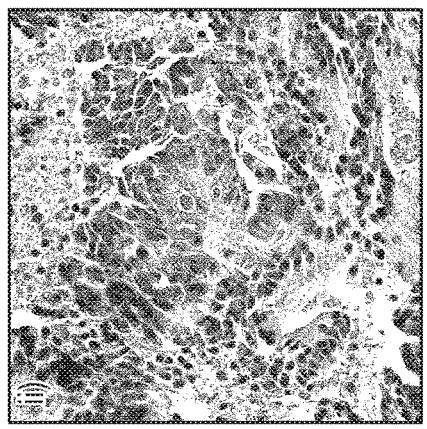
Figure 10E:
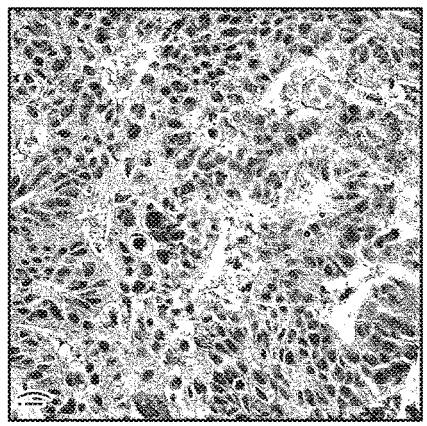

Viral replication was confirmed using RNAseq data. Replication was monitored by quantifying viral genome transcripts that mapped to the genome sequence of the infected virus in the RNA collected from patient biopsies. While viral gene expression was not identified in the RNA from tumor biopsies collected D2 or D8 from patients 1-11, the six viral gene transcripts (FIG. 10A) were highly expressed in the tumor of patient 12 on D2 with further increased expression on D8 post administration (FIG. 10C). Additionally, RNAseq quantification of IFNβ gene expression to monitor viral transgene expression confirmed viral replication occurred only in patient 12. No increase in IFN expression was detected in RNA from tumors D2 and D8 post treatment of patients 1-11. The IFNβ transgene, identified to be independent of endogenous IFNβ by aligning to the viral genome-transgene junction, was elevated D2 and D8 following virus administration in patient 12 only. The induction of IFN response was further validated by IFNβ serum ELISA in which the level of IFNβ in patient serum following virus administration was significantly greater in patient 12 than all other patients following virus administration (FIG. 10D). Together, analysis of viral genome and transgene expression and IFN production confirms replication occurred in the tumor of patient 12, but was not detectable in patients 1-11.

Differential Expression in Tumors with and without Viral Replication

In order to investigate the molecular basis and underlying transcriptional profile of the rapid virus replication and spreading observed in patient 12, comprehensive genome-wide transcript analysis using RNAseq data was conducted on tumor and surrounding normal tissue biopsies from all patients at baseline. Differential expression of transcripts in tumor relative to adjacent healthy liver (normal) biopsies was performed for all patients to investigate gene expression patterns unique to the tumor environment. Patterns of significantly differentially expressed genes (absolute value of the log 2 (fold change) [FC] of gene expression in tumor relative to normal tissue>1, FDR p-value<0.05) in the averaged non responsive tumor (patients 1-11) and responsive tumor (patient 12) were visualized using MA plots and heat maps (FIGS. 11A-D). Strikingly, more than half of the significantly differentially expressed genes in the tumor of patient 12 were down regulated, while the quantity and extent of downregulated genes in patients 1-11 is much less. This suggests the state of downregulation in the responding tumor was different than that in nonresponding tumors.

Interferon Signaling Gene Regulation

Since VSV was sensitive to IFN expression, and interferon-stimulated genes (ISG) play a role in controlling virus replication in cells, the extent of basal ISG differential expression was characterized for the responding tumor. The differentially expressed genes identified in the tumor relative to normal liver tissue of patient 12 using Ingenuity Pathway Analysis (IPA) were compared to the 1793 ISG gene set compiled from Interferome v2.0 and KEGG pathway databases. Within the differentially expressed genes of the responding tumor, 822 ISG were identified; 555 downregulated and 267 upregulated genes. The 555 downregulated ISG were subjected to pathway analysis to determine their role in host immune responses. Interestingly, pathways involved in triggering the antiviral state of cells, including dendritic cell maturation, antigen presentation, communication between innate and adaptive immune cells, crosstalk between dendritic cells and natural killer cells, IFN induction and signaling, and toll-like receptor signaling were in the top 20 most significantly implicated pathways (−log p-value=26.6-12.5). In contrast, none of the pathways identified to significantly involve the 267 ISG upregulated in the baseline tumor were critical for cellular responses to virus infection. This genomic profiling revealed that the baseline tumor existed in a state of downregulation, especially of ISG genes necessary for virus recognition and antiviral signaling. This was hypothesized to have created an environment permissive to virus replication.

Differential Gene Expression Across the Patient Population

Figure 11A:
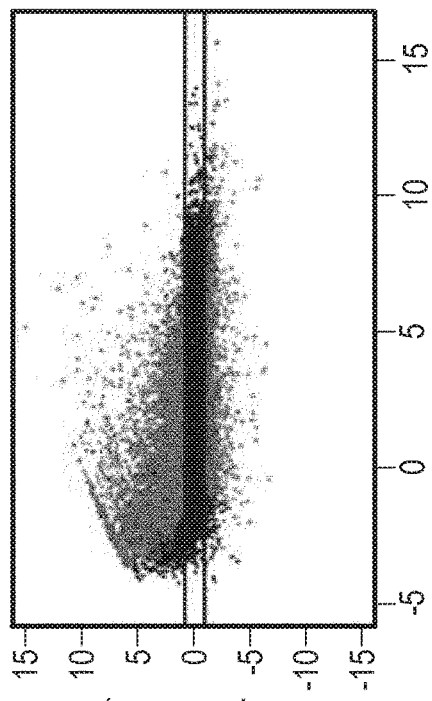
FIGS. 11A-D. Increased concentration of negative differential expression and standardized gene expression of antiviral response and antigen processing genes in responding tumor compared to nonresponding tumors. RNA sequencing was performed on the tumor samples and adjacent liver of all treated patients. (A) Comparison of differential expression (tumor vs. adjacent liver) vs. average reads in patients 1-11. (B) Patient 12 revealed a striking differences in the number of genes with significant negative differential expression. (C) The functional/variable antiviral gene set was used to profile the differential expression of tumor vs. adjacent normal genes in the treated patients. There was a larger concentration of negative differential expression of these genes in patient 12 than in patients 1-11. (D) The functional/variable antiviral gene set was used to profile the standardized gene expression (relative to treated population median). Again, there was a larger concentration of low standardized gene expression of these genes in patient 12. Expression of antiviral genes in patient 12 was both downregulated relative to adjacent liver and lower relative to the treated cancer population.
Figure 11B:
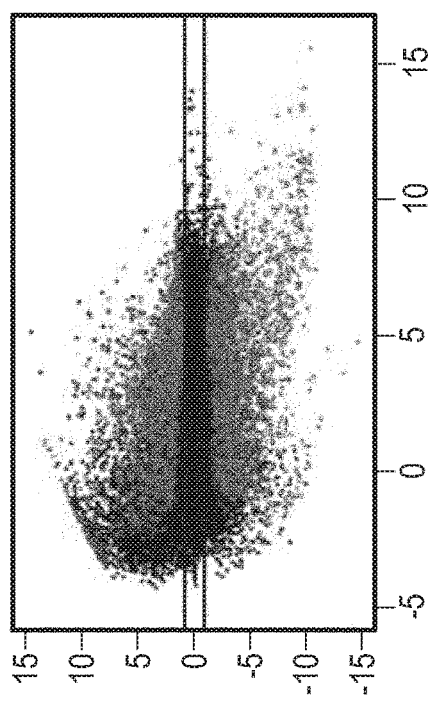
Figure 11C:
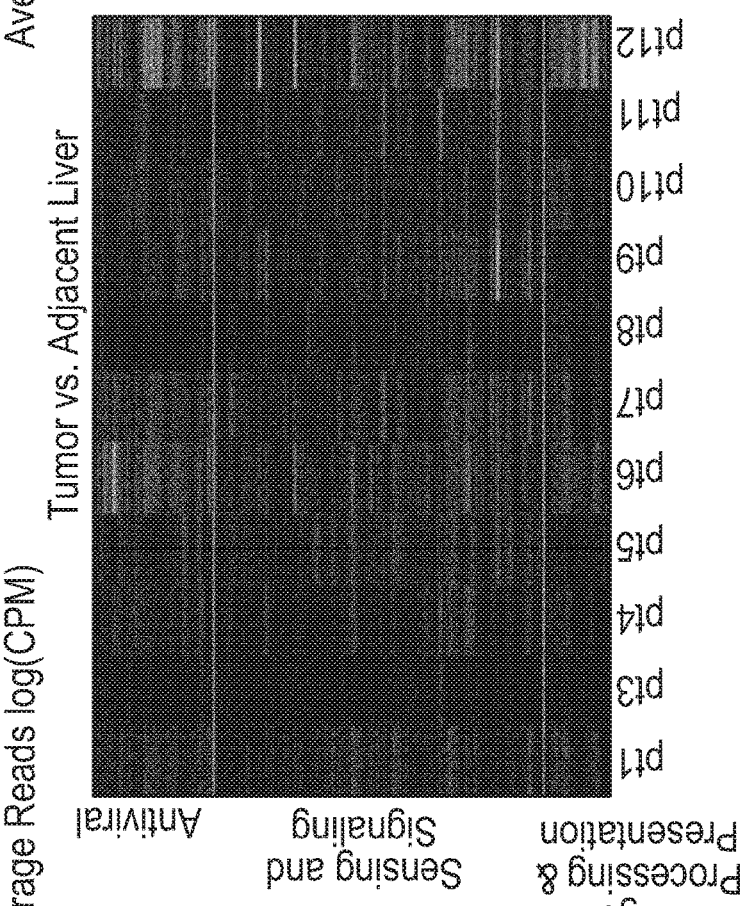
Figure 11D:
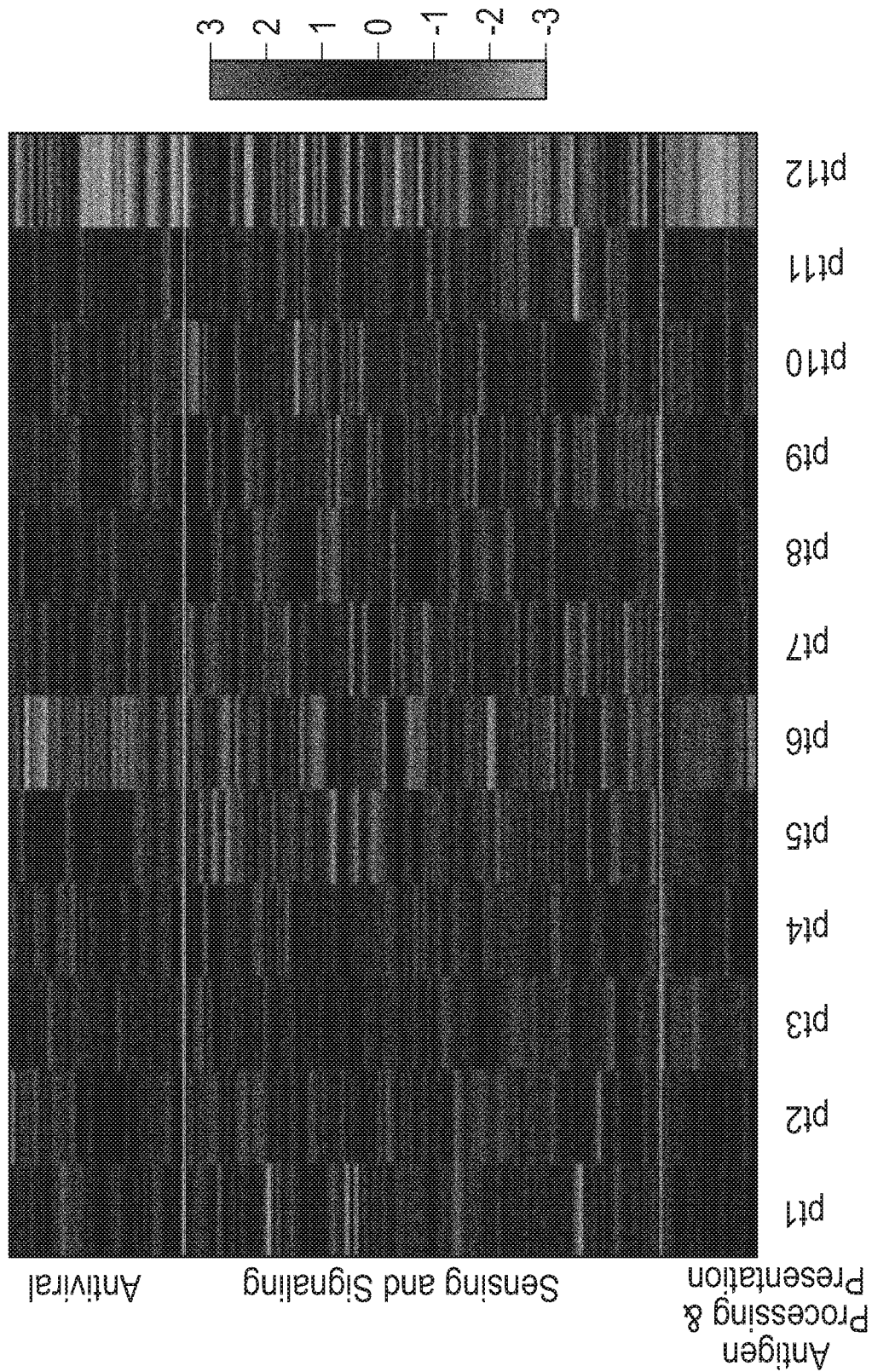

To better understand why replication occurred in the tumor of patient 12 but not in the tumors of patients 1-11, gene expression in all tumors at baseline was compared. To focus on relevant transcripts, the ISG pathway analysis above was used as a guide to select cellular mechanisms critical to virus sensing and control. Four antiviral cellular mechanisms were defined including 1) intrinsic antiviral responses, 2) virus sensing and signaling, and 3) antigen processing and presentation. It was hypothesized that defects in pathways contributing to these mechanisms defined using Interferome 2.0 and KEGG pathway database (including ISG, TLR signaling hsa04620, RIG-I signaling has04622, JAK/STAT pathways hsa04630, and antigen presentation hsa04612) would result in increased cellular susceptibility to viral infection. Comparison of gene expression across all baseline tumors using normalized expression standardized to the population median (z-score) revealed concentration of decreased gene expression in patient 12 relative to patients 1-11 (FIG. 11D). Differential expression analysis of baseline tumors relative to respective normal tissue also revealed more negative differentially expressed genes concentrated in patient 12 relative to patients 1-11 (FIG. 11C). Fischer exact tests determined the proportion of significantly downregulated genes (z<−1.96) in each antiviral pathway was significantly greater than the proportion of downregulated genes in the remaining genome for patient 12 but not for any of the other patients. This indicates that these pathways were uniquely and significantly enriched with genes of low expression in the responding tumor.

With patient 12 demonstrating deviation in gene expression relative to the rest of the study population, the baseline population used for identification of an antiviral gene signature was patients 1-11. Differentially expressed genes in the tumor of patient 12 relative to population baseline were identified using a z-score comparing RNA expression in patient 12 to the median expression in patients 1-11. From the pathways central to virus control, 74 genes (Table 2) were found to be downregulated using a standardized expression threshold of z<−1.5 in the tumor of patient 12 compared to the median baseline population.

These antiviral genes define a proprietary gene expression signature unique to the responding baseline tumor. These genes include genes involve in each of the three defined antiviral cellular pathways of Table 2, indicating defects in these pathways involved in controlling virus infection.

Figure 12:
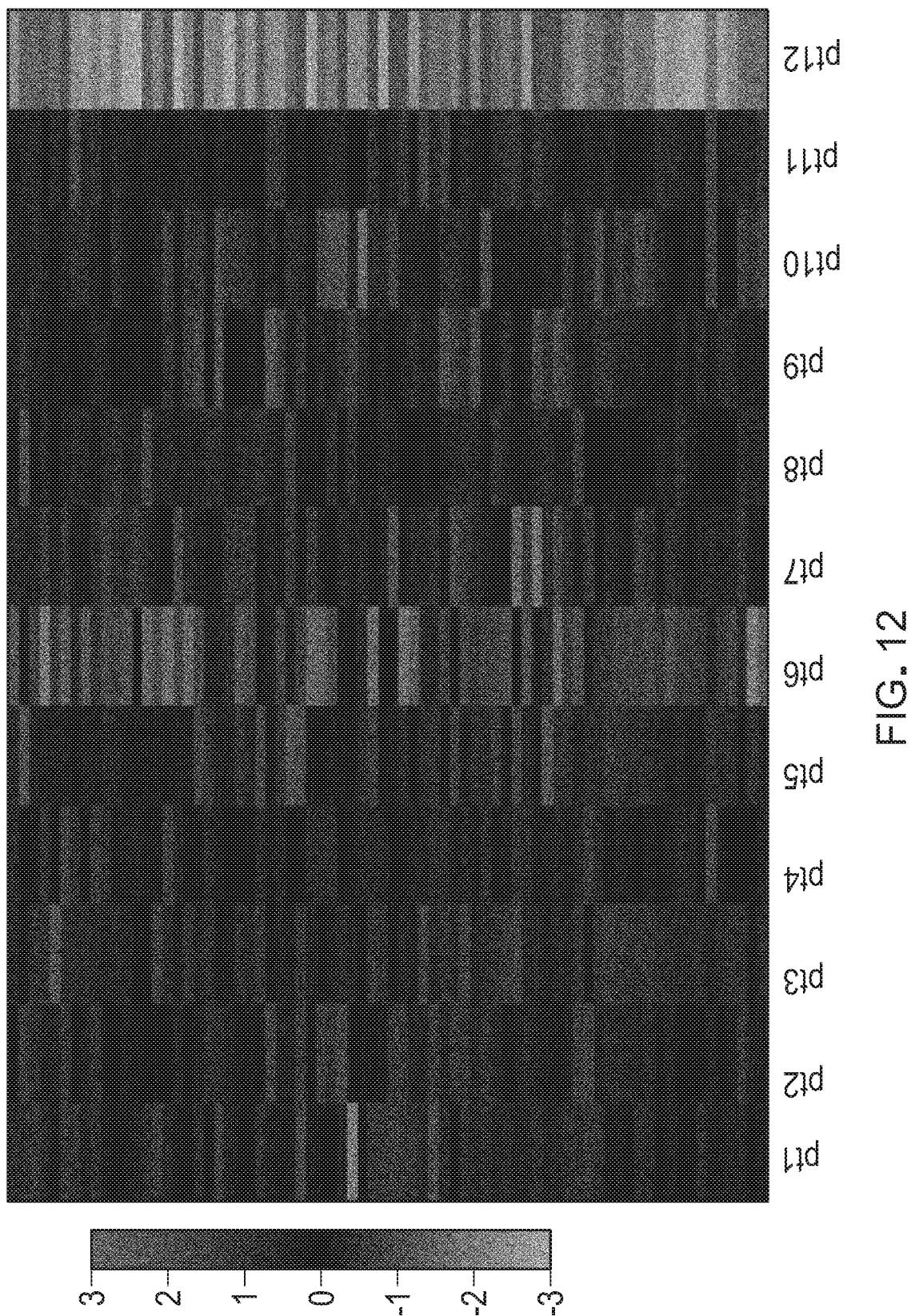
FIG. 12. Virus susceptibility genes involved in virus control and immune presentation are downregulated in responding tumor (selected as genes with standardized gene expression z<−1.5), revealing a set of genes with significantly lower expression than the population median (74 genes). See Table 2 for gene list and values for patient #12.

Comparison of normalized expression levels and standardized expression levels of these genes, in the baseline tumor biopsies across all patients further revealed low gene expression of the majority of the gene set in patient 12 while gene expression levels were noticeably higher in patients 1-11 (FIG. 12). This demonstrates the tumor of patient 12 was defective (negatively differentially expressed) in antiviral pathways involved in controlling infection while the tumors in other patients were not. Therefore, the low gene expression of these 74 genes was unique to the baseline tumor of patient 12 (for this population of 12 patients) and may explain the exceptional susceptibility of this tumor to virus replication.

Viral Susceptibility Gene Signature

Figures 13A, 13B:
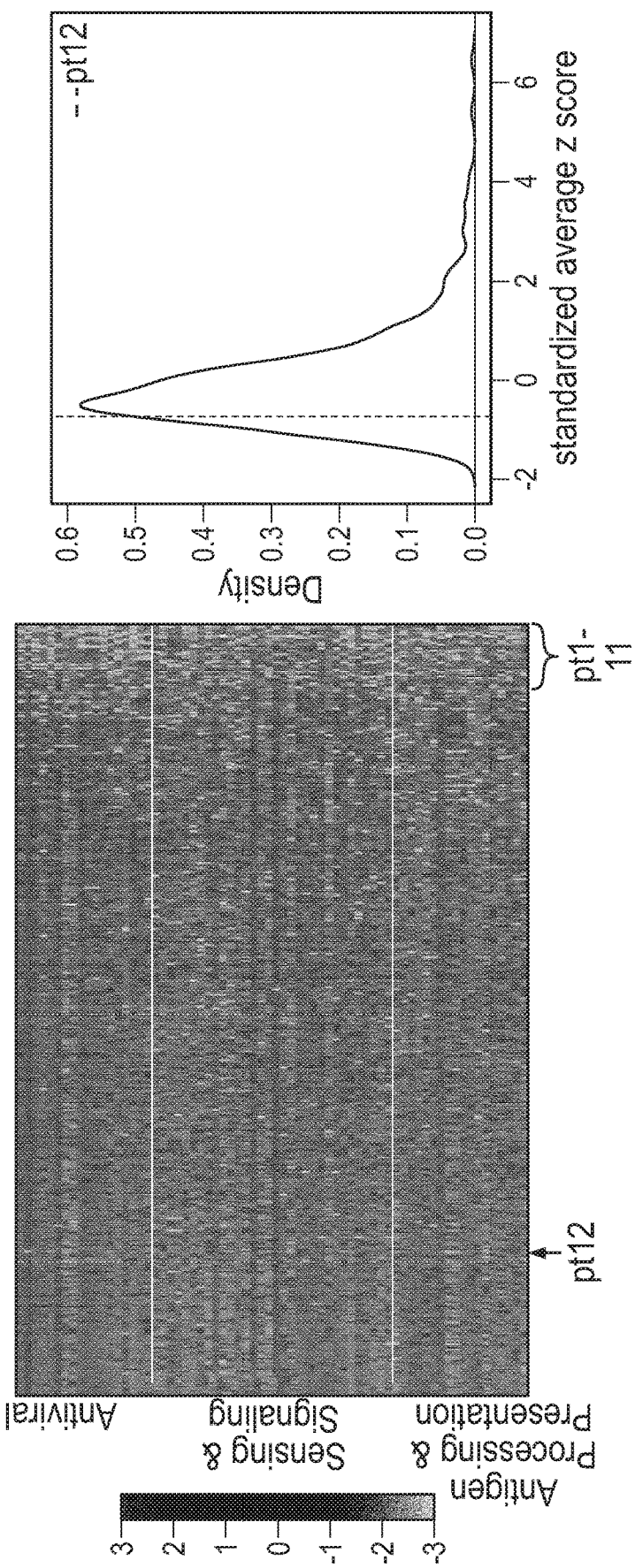
FIGS. 13A-B. Gene expression profiling of genes involved in virus control and immune presentation across patients on phase 1 VSV-IFNβ trial and similar cancers from the TCGA database. RNAseq data was obtained from liver and colorectal cancer patients and the patients provided herein, and alignment free quantification and normalization were performed. (A) Standardized expression (relative to mean expression of the same gene in the whole population) of antiviral geneset in liver cancer, colorectal cancer, and current clinical trial patients. Columns were ordered by cumulative sum of standardized expression. Patient 12 was clearly separated from other patients treated with VSV-IFNβ. (B) Distribution of the average standardized gene expression revealed that patient 12 was not an extreme outlier, but that other tumors may have a similar or more extreme profile of these genes.

To determine if the expression pattern of this antiviral gene set in patient 12 was an outlier or could be used to identify subsets of virus-susceptible patients with similar expression patterns from large cohorts, the gene expression profile relative to population mean was analyzed for large cancer cohorts available from the TCGA database. The liver cancer TCGA cohort was assessed since the current trial was designed to treat patients with primary liver cancer or cancer metastatic to the liver. The colon and renal adenocarcinoma TCGA cohort was assessed since patient 12 was a colorectal cancer patient with liver metastases. Raw sequencing data from these patients and the 12 patients treated on the phase 1 trial with VSV-IFNβ analyzed using alignment free quantification and normalization. For each patient in the cohorts and on the trial, the expression of each gene within the gene signature was standardized to the population mean and standard deviation. A standardized expression score was calculated for each patient by averaging standardized gene expression across the gene set. To place patient 12 in the context of the larger cancer cohort, a heat map was generated to visualize the distribution of standardized gene expression. Patients (each column) were ordered by cumulative standardized gene expression, in which patient 12 was clearly separated for other patients treated with VSV-IFNβ (FIG. 13A).

In the current analysis of alignment free expression, patient 12 had an average standardized expression score of −0.73. The distribution of the average standardized expression score for TCGA liver and colorectal populations was shown in FIG. 13B, with the vertical line demonstrating the average standardized expression for patient 12. In both the heatmap of standardized gene expression and the plot of average standardized gene expression distribution, it was clear that there were cancer patients with decreased expression of the identified gene set as extreme or more extreme than patient 12 (FIG. 13). The tumors of these patients may be more susceptible than other tumors within the population to virus replication. While patient 12 appeared to be an extreme outlier within the current clinical trial, gene signature expression analysis suggested that there were subsets of cancer populations with tumors more susceptible to virus replication, and this set of 74 genes can be used to identify such patients.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer in a mammal, wherein said method comprises:
   (a) identifying said mammal as having cancer cells that express:
   (1) a low level of a majority of the genes selected from the Gene Set 1 group consisting of IFI27, IFI27L1, IFI30, IFI6, IFI35, IFI16, IFI44, IFIT3, IFIT2, IFIT1, IFIT1B, IFIT5, IFITM3, TRIM14, TRIM69, TRIM21, TRIM25, TRIM39, TRIM5, TRIM26, TRIM47, OASL, OAS2 and MX1, as compared to expression by healthy control cells of the same tissue type as the cancer cells;
   (2) a low level of a majority of the genes selected from the Gene Set 2 group consisting of DDX60, DDX60L, DHX58, DDX58, ISG15, IFIH1, CD14, LBP, TLR4, MYD88, TOLLIP, TLR3, TLR5, TLR6, TLR9, TICAM1, IRF7, IRF5, MAPK11, APK12, MAPK8, RIPK1, IKBKG and NFKBIA, as compared to expression by healthy control cells of the same tissue type as the cancer cells;
   (3) a low level of a majority of the genes selected from the Gene Set 3 group consisting of IFNAR1, IFNAR2, IFNGD1, IRF1, JAK1, STAT1, STAT2, STAT3, STAT5A, IRF9, PIK3R2, PIK3CG, AKT1, AKT2, AKT3 and MTOR, as compared to expression by healthy control cells of the same tissue type as the cancer cells; and
   (4) a low level of a majority of the genes selected from the Gene Set 4 group consisting of PSMB8, PSMB9, PSMB10, PSME1, PSME2, TAP1, TAP2, TAPBP, TAPBPL, ERAP1, ERAP2, CALR, PDIA3, HLA-A, HLA-B, HLA-C, BTN3A1, BTN3A2, BTN3A3 and B2M, as compared to expression by healthy control cells of the same tissue type as the cancer cells; and (b) administering an oncolytic virus to said mammal under conditions wherein the number of cancer cells within the mammal is reduced.

2. The method of claim 1, wherein said mammal is a human.

3. The method of claim 1, wherein said cancer is liver cancer.

4. The method of claim 1, wherein said oncolytic virus is VSV-IFNβ.

5. The method of claim 1, wherein said method comprises administering said oncolytic virus to said mammal no more than one time.

6. A method for treating cancer in a mammal, wherein said method comprises:
(a) identifying said mammal as having cancer cells that lack:
(1) low expression of at least 50 percent of the genes selected from the Gene Set 1 group consisting of IFI27, IFI27L1, IFI30, IFI6, IFI35, IFI16, IFI44, IFIT3, IFIT2, MIT1, IFIT1B, IFIT5, IFITM3, TRIM14, TRIM69, TRIM21, TRIM25, TRIM39, TRIMS, TRIM26, TRIM47, OASL, OAS2 and MX1, as compared to expression by healthy control cells of the same tissue type as the cancer cells;
(2) low expression of at least 50 percent of the genes selected from the Gene Set 2 group consisting of DDX60, DDX60L, DHX58, DDX58, ISG15, IFIH1, CD14, LBP, TLR4, MYD88, TOLLIP, TLR3, TLR5, TLR6, TLR9, TICAM1, IRF7, IRF5, MAPK11, APK12, MAPK8, RIPK1, IKBKG and NFKBIA, as compared to expression by healthy control cells of the same tissue type as the cancer cells;
(3) low expression of at least 50 percent of the genes selected from the Gene Set 3 group consisting of IFNAR1, IFNAR2, IFNGD1, IRF1, JAK1, STAT1, STAT2, STAT3, STAT5A, IRF9, PIK3R2, PIK3CG, AKT1, AKT2, AKT3 and MTOR, as compared to expression by healthy control cells of the same tissue type as the cancer cells; and
(4) low expression of at least 50 percent of the genes selected from the Gene Set 4 group consisting of PSMB8, PSMB9, PSMB10, PSME1, PSME2, TAP1, TAP2, TAPBP, TAPBPL, ERAP1, ERAP2, CALR, PDIA3, HLA-A, HLA-B, HLA-C, BTN3A1, BTN3A2, BTN3A3 and B2M, as compared to expression by healthy control cells of the same tissue type as the cancer cells; and
(b) administering an oncolytic virus to said mammal at a dose of $1\times10^9$ TCID$_{50}$ or greater at least once every two to four weeks for a total of at least two administration to induce an immune response against said cancer, wherein the number of cancer cells within the mammal is reduced.

7. The method of claim 6, wherein said mammal is a human.

8. The method of claim 6, wherein said cancer is liver cancer.

9. The method of claim 6, wherein said oncolytic virus is VSV-IFNβ.

10. The method of claim 6, wherein said method comprises administering said oncolytic virus to said mammal at least three times.

11. A method for treating cancer in a mammal, wherein said method comprises:
(a) identifying said mammal as having cancer cells that lack:
(1) low expression of at least 50 percent of the genes selected from the Gene Set 5 group consisting of MX1, MX2, OAS2, OASL, APOBEC3G, ISG15, GBP2, IRF2, MAP3K14, MOV10 and RTP4, as compared to expression by healthy control cells of the same tissue type as the cancer cells;
(2) low expression of at least 50 percent of the genes selected from the Gene Set 6 group consisting of DDX60, NFKBIA, MAPK8, MAPK11, MAPK12, TRAF3, DHX58, IKBKG, RIPK1, AKT3, TAB1, TICAM1, PIK3R5, IFNAR2, TICAM2, IRF5, MYD88, PIK3CG, TLR9, TOLLIP, TLR3, TLR4, TLR5, PIK3R3, CD14, CASP1, STAM2, IRF9, FHL1, MTOR, STAT2, STAT3 and STAT5A, as compared to expression by healthy control cells of the same tissue type as the cancer cells; and
(3) low expression of at least 50 percent of the genes selected from the Gene Set 7 group consisting of PDIA3, HLA-A, HLA-B, HLA-C, HLA-E, HLA-F, B2M, PSME1, PSME2, TAP1, TAP2, TAPBP, CALR, PSMB8, PSMB9, ERAP1, ERAP2 and TAPBPL, as compared to expression by healthy control cells of the same tissue type as the cancer cells; and
(b) administering an oncolytic virus to said mammal at a dose of $1\times10^9$ TCID$_{50}$ or greater at least once every two to four weeks for a total of at least two administration to induce an immune response against said cancer, wherein the number of cancer cells within the mammal is reduced.

12. The method of claim 11, wherein said mammal is a human.

13. The method of claim 11, wherein said cancer is liver cancer.

14. The method of claim 11, wherein said oncolytic virus is VSV-IFNβ.

15. The method of claim 11, wherein said method comprises administering said oncolytic virus to said mammal at least three times.

16. A method for treating cancer in a mammal, wherein said method comprises:
(a) identifying said mammal as having cancer cells that express:
(1) a low level of a majority of the genes selected from the Gene Set 5 group consisting of MX1, MX2, OAS2, OASL, APOBEC3G, ISG15, GBP2, IRF2, MAP3K14, MOV10 and RTP4, as compared to expression by healthy control cells of the same tissue type as the cancer cells;
(2) a low level of a majority of the genes selected from the Gene Set 6 group consisting of DDX60, NFKBIA, MAPK8, MAPK11, MAPK12, TRAF3, DHX58, IKBKG, RIPK1, AKT3, TAB1, TICAM1, PIK3R5, IFNAR2, TICAM2, IRF5, MYD88, PIK3CG, TLR9, TOLLIP, TLR3, TLR4, TLR5, PIK3R3, CD14, CASP1, STAM2, IRF9, FHL1, MTOR, STAT2, STAT3 and STAT5A, as compared to expression by healthy control cells of the same tissue type as the cancer cells; and
(3) a low level of a majority of the genes selected from the Gene Set 7 group consisting of PDIA3, HLA-A, HLA-B, HLA-C, HLA-E, HLA-F, B2M, PSME1, PSME2, TAP1, TAP2, TAPBP, CALR, PSMB8, PSMB9, ERAP1, ERAP2 and TAPBPL, as compared to expression by healthy control cells of the same tissue type as the cancer cells; and (b) administering an oncolytic virus to said mammal under conditions, wherein the number of cancer cells within the mammal is reduced.

17. The method of claim 16, wherein said mammal is a human.

18. The method of claim 16, wherein said cancer is liver cancer.

19. The method of claim 16, wherein said oncolytic virus is VSV-IFNβ.

20. The method of claim 16, wherein said method comprises administering said oncolytic virus to said mammal no more than one time.

* * * * *